United States Patent
Chen et al.

(10) Patent No.: US 12,115,190 B2
(45) Date of Patent: Oct. 15, 2024

(54) IRF-4 ENGINEERED T CELLS AND USES THEREOF IN TREATING CANCER

(71) Applicant: , Houston, TX (US)

(72) Inventors: Wenhao Chen, Houston, TX (US); Xian Chang Li, Houston, TX (US)

(73) Assignee: THE METHODIST HOSPITAL, Houston, TX (US)

( * ) Notice: Subject to any disclaimer, the term of this patent is extended or adjusted under 35 U.S.C. 154(b) by 998 days.

(21) Appl. No.: 16/975,933

(22) PCT Filed: Feb. 27, 2019

(86) PCT No.: PCT/US2019/019745
§ 371 (c)(1),
(2) Date: Aug. 26, 2020

(87) PCT Pub. No.: WO2019/168914
PCT Pub. Date: Sep. 6, 2019

(65) Prior Publication Data
US 2020/0405763 A1 Dec. 31, 2020

Related U.S. Application Data

(60) Provisional application No. 62/635,846, filed on Feb. 27, 2018.

(51) Int. Cl.
| | |
|---|---|
| *A61K 35/17* | (2015.01) |
| *A61K 38/20* | (2006.01) |
| *A61K 39/00* | (2006.01) |
| *A61K 39/395* | (2006.01) |
| *A61K 45/06* | (2006.01) |
| *A61P 35/00* | (2006.01) |
| *C07K 14/47* | (2006.01) |
| *C07K 16/28* | (2006.01) |
| *C12N 5/0783* | (2010.01) |
| *C12N 15/86* | (2006.01) |

(52) U.S. Cl.
CPC .......... *A61K 35/17* (2013.01); *A61K 38/2013* (2013.01); *A61K 39/3955* (2013.01); *A61K 45/06* (2013.01); *A61P 35/00* (2018.01); *C07K 14/4702* (2013.01); *C07K 16/2827* (2013.01); *C12N 5/0638* (2013.01); *C12N 15/86* (2013.01); *A61K 2039/505* (2013.01); *C12N 2740/10043* (2013.01)

(58) Field of Classification Search
None
See application file for complete search history.

(56) References Cited

U.S. PATENT DOCUMENTS

| | | | |
|---|---|---|---|
| 2010/0203056 A1* | 8/2010 | Irving | C07K 16/3046 435/69.6 |
| 2011/0306517 A1 | 12/2011 | Feldman et al. | |
| 2015/0209388 A1* | 7/2015 | Yi | A61K 31/675 435/375 |
| 2016/0058852 A1 | 3/2016 | Ter Meulen et al. | |

FOREIGN PATENT DOCUMENTS

WO 2017075465 A1 5/2017

OTHER PUBLICATIONS

Koh, Choong-Hyun, et al. "CD8 T-cell subsets: heterogeneity, functions, and therapeutic potential." Experimental & Molecular Medicine 55.11 (2023): 2287-2299. (Year: 2023).*
Yao, et al., Interferon Regulatory Factor 4 Sustains CD8+ T Cell Expansion and Effector Differentiation, Immunity, Nov. 14, 2013, vol. 39, No. 5, pp. 833-845.
Marecki, et al., Differential expression and distinct functions of IFN regulatory factor 4 and IFN consensus sequence binding protein in macrophages, Journal of Immunology, Sep. 1, 1999, vol. 163, No. 5, pp. 2713-2722.
Roszkowski et al., Simultaneous Generation of CD8+ and CD4+ Melanoma-Reactive T Cells by Retroviral-Mediated Transfer of a Single T-Cell Receptor, Cancer Research, Feb. 15, 2005, vol. 65, No. 4, pp. 1570-1576.
Shin, et al., Enhanced Anti-tumor Reactivity of Cytotoxic T Lymphocytes Expressing PD-1 Decoy, Immune Network, Epub Apr. 28, 2016, vol. 16, No. 2, pp. 134-139.
Wu, et al., Ablation of Transcription Factor IRF4 Promotes Transplant Acceptance by Driving Allogenic CD4+ T Cell Dysfunction, Immunity, Dec. 19, 2017, Epub Dec. 5, 2017, vol. 47, No. 6, pp. 1114-1128.
Qian, et al., Interferon regulatory factor 4 (IRF4) is overexpressed in human non-small cell lung cancer (NSCLC) and activates the Notch signaling pathway, Molecular Medicine Reports, Nov. 2017, Epub Aug. 22, 2017, vol. 16, No. 5, pp. 6034-6040.

(Continued)

*Primary Examiner* — Robert J Yamasaki
(74) *Attorney, Agent, or Firm* — Meunier Carlin & Curfman LLC

(57) ABSTRACT

Methods to treat cancer in a subject comprising administering to the subject a therapeutically effective amount of T-cells of the subject having increased IRF4 polypeptide expression compared to a control are disclosed. Also disclosed are methods of increasing tumor reactivity of a T-cell by increasing IRF4 polypeptide expression, and methods to predict the likelihood that a subject having cancer will respond therapeutically to administered T-cells having increased IRF4 polypeptide expression. Also disclosed are compositions comprising a T-cell and a viral vector encoding an IRF4 polypeptide. The compositions are methods are useful for treating numerous cancers in which higher level expression of IRF4 in T-cells would be beneficial. In some embodiments, activated tumor specific T-cells having increased IRF4 expression have greater infiltration in tumors and enhanced local immunological responses.

14 Claims, 8 Drawing Sheets

Specification includes a Sequence Listing.

(56) References Cited

OTHER PUBLICATIONS

International Search Report and Written Opinion for International Application No. PCT/US2019/019745 mailed Jun. 10, 2019.
International Preliminary Report on Patentability issued for Application No. PCT/US2019/019745, dated Aug. 3, 2020.
Aki S., et al., High-Pressure Phase Behavior of Carbon Dioxide with Imidazolium-Based Ionic Liquids, J. Phys. Chem. B (2004) 20355-20365.
Lin, H, B.D. Freeman, Permeation and diffusion, in: H. Czichos, L. Smith, T. Saito (Eds.), Springer-handb. Mater. Meas. Methods, Springer, 2006, pp. 371-387.
Merkel T., et al., Silver salt facilitated transport membranes for olefin/paraffin separations: Carrier instability and a novel regeneration method, J. Memb. Sci. 447 (2013) 177-189.
Alhamad, T., Venkatachalam, K., Linette, G.P., and Brennan, D.C. (2016). Checkpoint inhibitors in kidney transplant recipients and the potential risk of rejection. Am. J. Transplant. 16, 1332-1333.
Bally, A.P., Austin, J.W., and Boss, J.M. (2016). Genetic and epigenetic regulation of PD-1 expression. J. Immunol. 196, 2431-2437.
Baumeister, S.H., Freeman, G.J., Dranoff, G., and Sharpe, A.H. (2016). Coinhibitory pathways in immunotherapy for cancer. Annu. Rev. Immunol. 34, 539-573.
Bollig, N., Br€ustle, A., Kellner, K., Ackermann, W., Abass, E., Raifer, H., Camara, B., Brendel, C., Giel, G., Bothur, E., et al. (2012). Transcription factor IRF4 determines germinal center formation through follicular T-helper cell differentiation. Proc. Natl. Acad. Sci. USA 109, 8664-8669.
Bolton, E.M., Gracie, J.A., Briggs, J.D., Kampinga, J., and Bradley, J.A. (1989). Cellular requirements for renal allograft rejection in the athymic nude rat. J. Exp. Med. 169, 1931-1946.
Brustle, A., Heink, S., Huber, M., Rosenpl€anter, C., Stadelmann, C., Yu, P., Arpaia, E., Mak, T.W., Kamradt, T., and Lohoff, M. (2007). The development of inflammatory T(H)-17 cells requires interferon-regulatory factor 4. Nat. Immunol. 8, 958-966.
Chen, W., Diao, J., Stepkowski, S.M., and Zhang, L. (2007). Both infiltrating regulatory T cells and insufficient antigen presentation are involved in longterm cardiac xenograft survival. J. Immunol. 179, 1542-1548.
Conlon, T.M., Saeb-Parsy, K., Cole, J.L., Motallebzadeh, R., Qureshi, M.S., Rehakova, S., Negus, M.C., Callaghan, C.J., Bolton, E.M., Bradley, J.A., and Pettigrew, G.J. (2012). Germinal center alloantibody responses are mediated exclusively by indirect-pathway CD4 T follicular helper cells. J. Immunol. 188, 2643-2652.
Crawford, A., Angelosanto, J.M., Kao, C., Doering, T.A., Odorizzi, P.M., Barnett, B.E., and Wherry, E.J. (2014). Molecular and transcriptional basis of CD4.T cell dysfunction during chronic infection. Immunity 40, 289-302.
Cretney, E., Xin, A., Shi, W., Minnich, M., Masson, F., Miasari, M., Belz, G.T., Smyth, G.K., Busslinger, M., Nutt, S.L., and Kallies, A. (2011). The transcription factors Blimp-1 and IRF4 jointly control the differentiation and function of effector regulatory T cells. Nat. Immunol. 12, 304-311.
Fathman, C.G., and Lineberry, N.B. (2007). Molecular mechanisms of CD4+ T-cell anergy. Nat. Rev. Immunol. 7, 599-609.
Grumont, R.J., and Gerondakis, S. (2000). Rel induces interferon regulatory factor 4 (IRF-4) expression in lymphocytes: modulation of interferon-regulated gene expression by rel/nuclear factor kappaB. J. Exp. Med. 191, 1281-1292.
Grusdat, M., McIlwain, D.R., Xu, H.C., Pozdeev, V.I., Knievel, J., Crome, S.Q., Robert-Tissot, C., Dress, R.J., Pandyra, A.A., Speiser, D.E., et al. (2014). IRF4 and BATF are critical for CD8₊T-cell function following infection with LCMV. Cell Death Differ. 21, 1050-1060.
Gupta, S., Balasubramanian, S., Thornley, T.B., Strom, T.B., and Kenny, J.J. (2011). Direct pathway T-cell alloactivation is more rapid than indirect pathway alloactivation. Transplantation 91, e65-e67.
Huber, M., and Lohoff, M. (2014). IRF4 at the crossroads of effector T-cell fate decision. Eur. J. Immunol. 44, 1886-1895.

Huber, M., Br€ustle, A., Reinhard, K., Guralnik, A., Walter, G., Mahiny, A., von Lo¨ w, E., and Lohoff, M. (2008). IRF4 is essential for IL-21-mediated induction, amplification, and stabilization of the Th17 phenotype. Proc. Natl. Acad. Sci. USA 105, 20846-20851.
Kim, H.J., Barnitz, R.A., Kreslavsky, T., Brown, F.D., Moffett, H., Lemieux, M.E., Kaygusuz, Y., Meissner, T., Holderried, T.A., Chan, S., et al. (2015). Stable inhibitory activity of regulatory T cells requires the transcription factor Helios. Science 350, 334-339.
Krieger, N.R., Yin, D.P., and Fathman, C.G. (1996). CD4+ but not CD8+ cells are essential for allorejection. J. Exp. Med. 184, 2013-2018.
Larkin, J., Chiarion-Sileni, V., Gonzalez, R., Grob, J.J., Cowey, C.L., Lao, C.D., Schadendorf, D., Dummer, R., Smylie, M., Rutkowski, P., et al. (2015). Combined nivolumab and ipilimumab or monotherapy in untreated melanoma. N. Engl. J. Med. 373, 23-34.
Lechler, R.I., Sykes, M., Thomson, A.W., and Turka, L.A. (2005). Organ transplantation—how much of the promise has been realized? Nat. Med. 11, 605-613.
Lee, Y., Awasthi, A., Yosef, N., Quintana, F.J., Xiao, S., Peters, A., Wu, C., Kleinewietfeld, M., Kunder, S., Hafler, D.A., et al. (2012). Induction and molecular signature of pathogenic TH17 cells. Nat. Immunol. 13, 991-999.
Li, P., Spolski, R., Liao, W., Wang, L., Murphy, T.L., Murphy, K.M., and Leonard, W.J. (2012). BATF-JUN is critical for IRF4-mediated transcription in T cells. Nature 490, 543-546.
Lipson, E.J., Bagnasco, S.M., Moore, J., Jr., Jang, S., Patel, M.J., Zachary, A.A., Pardoll, D.M., Taube, J.M., and Drake, C.G. (2016). Tumor regression and allograft rejection after administration of anti-PD-1. N. Engl. J. Med. 374, 896-898.
Liu, Z., Fan, H., and Jiang, S. (2013). CD4(+) T-cell subsets in transplantation. Immunol. Rev. 252, 183-191.
Mahnke, J., Schumacher, V., Ahrens, S., K€ading, N., Feldhoff, L.M., Huber, M., Rupp, J., Raczkowski, F., and Mittr€ucker, H.W. (2016). Interferon regulatory factor 4 controls TH1 cell effector function and metabolism. Sci. Rep. 6, 35521.
Man, K., Miasari, M., Shi, W., Xin, A., Henstridge, D.C., Preston, S., Pellegrini, M., Belz, G.T., Smyth, G.K., Febbraio, M.A., et al. (2013). The transcription factor IRF4 is essential for TCR affinity-mediated metabolic programming and clonal expansion of T cells. Nat. Immunol. 14, 1155-1165.
Martinez, R.J., Zhang, N., Thomas, S.R., Nandiwada, S.L., Jenkins, M.K., Binstadt, B.A., and Mueller, D.L. (2012). Arthritogenic self-reactive CD4+ T cells acquire an FR4hiCD73hi anergic state in the presence of Foxp3+ regulatory T cells. J. Immunol. 188, 170-181.
Mittrucker, H.W., Matsuyama, T., Grossman, A., K€undig, T.M., Potter, J., Shahinian, A., Wakeham, A., Patterson, B., Ohashi, P.S., and Mak, T.W. (1997). Requirement for the transcription factor LSIRF/IRF4 for mature B and T lymphocyte function. Science 275, 540-543.
Miyahara, Y., Khattar, M., Schroder, P.M., Mierzejewska, B., Deng, R., Han, R., Hancock, W.W., Chen, W., and Stepkowski, S.M. (2012). Anti-TCRb mAb induces long-term allograft survival by reducing antigen-reactive T cells and sparing regulatory T cells. Am. J. Transplant. 12, 1409-1418.
Murphy, T.L., Tussiwand, R., and Murphy, K.M. (2013). Specificity through cooperation: BATF-IRF interactions control immune-regulatory networks. Nat. Rev. Immunol. 13, 499-509.
Nayar, R., Enos, M., Prince, A., Shin, H., Hemmers, S., Jiang, J.K., Klein, U., Thomas, C.J., and Berg, L.J. (2012). TCR signaling via Tec kinase ITK and interferon regulatory factor 4 (IRF4) regulates CD8+ T-cell differentiation. Proc. Natl. Acad. Sci. USA 109, E2794-E2802.
Notarangelo, L.D. (2013). Functional T cell immunodeficiencies (with T cells present). Annu. Rev. Immunol. 31, 195-225.
Ochiai, K., Maienschein-Cline, M., Simonetti, G., Chen, J., Rosenthal, R., Brink, R., Chong, A.S., Klein, U., Dinner, A.R., Singh, H., and Sciammas, R. (2013). Transcriptional regulation of germinal center B and plasma cell fates by dynamical control of IRF4. Immunity 38, 918-929.
Postow, M.A., Chesney, J., Pavlick, A.C., Robert, C., Grossmann, K., McDermott, D., Linette, G.P., Meyer, N., Giguere, J.K., Agarwala,

(56) References Cited

OTHER PUBLICATIONS

S.S., et al. (2015). Nivolumab and ipilimumab versus ipilimumab in untreated melanoma. N. Engl. J. Med. 372, 2006-2017.
Rangachari, M., and Kuchroo, V.K. (2013). Using EAE to better understand principles of immune function and autoimmune pathology. J. Autoimmun. 45, 31-39.
Rogers, N.J., and Lechler, R.I. (2001). Allorecognition. Am. J. Transplant. 1, 97-102.
Ross, E.M., Bourges, D., Hogan, T.V., Gleeson, P.A., and van Driel, I.R. (2014). Helios defines T cells being driven to tolerance in the periphery and thymus. Eur. J. Immunol. 44, 2048-2058.
Safinia, N., Scotta, C., Vaikunthanathan, T., Lechler, R.I., and Lombardi, G. (2015). Regulatory T cells: serious contenders in the promise for immunological tolerance in transplantation. Front. Immunol. 6, 438.
Schietinger, A., and Greenberg, P.D. (2014). Tolerance and exhaustion: defining mechanisms of T cell dysfunction. Trends Immunol. 35, 51-60.
Schietinger, A., Philip, M., Krisnawan, V.E., Chiu, E.Y., Delrow, J.J., Basom, R.S., Lauer, P., Brockstedt, D.G., Knoblaugh, S.E., H€ammerling, G.J., et al. (2016). Tumor-specific T cell dysfunction is a dynamic antigen-driven differentiation program initiated early during tumorigenesis. Immunity 45, 389-401.
Singer, M., Wang, C., Cong, L., Marjanovic, N.D., Kowalczyk, M.S., Zhang, H., Nyman, J., Sakuishi, K., Kurtulus, S., Gennert, D., et al. (2016). A distinct gene module for dysfunction uncoupled from activation in tumor-infiltrating T cells. Cell 166, 1500-1511. e9.
Staudt, V., Bothur, E., Klein, M., Lingnau, K., Reuter, S., Grebe, N., Gerlitzki, B., Hoffmann, M., Ulges, A., Taube, C., et al. (2010). Interferon-regulatory factor 4 is essential for the developmental program of T helper 9 cells. Immunity 33, 192-202.
Vander Lugt, B., Khan, A.A., Hackney, J.A., Agrawal, S., Lesch, J., Zhou, M., Lee, W.P., Park, S., Xu, M., DeVoss, J., et al. (2014). Transcriptional programming of dendritic cells for enhanced MHC class II antigen presentation. Nat. Immunol. 15, 161-167.
Wherry, E.J., and Kurachi, M. (2015). Molecular and cellular insights into T cell exhaustion. Nat. Rev. Immunol. 15, 486-499.
Xiao, X., Shi, X., Fan, Y., Wu, C., Zhang, X., Minze, L., Liu, W., Ghobrial, R.M., Lan, P., and Li, X.C. (2016). The costimulatory receptor OX40 inhibits interleukin-17 expression through activation of repressive chromatin remodeling pathways. Immunity 44, 1271-1283.
Yang, H., Thomas, D., Boffa, D.J., Ding, R., Li, B., Muthukumar, T., Sharma, V.K., Lagman, M., Luo, G.X., Kapur, S., et al. (2002). Enforced c-REL deficiency prolongs survival of islet allografts1. Transplantation 74, 291-298.
Yao, S., Buzo, B.F., Pham, D., Jiang, L., Taparowsky, E.J., Kaplan, M.H., and Sun, J. (2013). Interferon regulatory factor 4 sustains CD8(+) T cell expansion and effector differentiation. Immunity 39, 833-845.
Yuan, X., Paez-Cortez, J., Schmitt-Knosalla, I., D' Addio, F., Mfarrej, B., Donnarumma, M., Habicht, A., Clarkson, M.R., Iacomini, J., Glimcher, L.H., et al. (2008). A novel role of CD4 Th17 cells in mediating cardiac allograft rejection and vasculopathy. J. Exp. Med. 205, 3133-3144.
Zarour, H.M. (2016). Reversing T-cell dysfunction and exhaustion in cancer. Clin. Cancer Res. 22, 1856-1864.
Zheng, Y., Chaudhry, A., Kas, A., deRoos, P., Kim, J.M., Chu, T.T., Corcoran, L., Treuting, P., Klein, U., and Rudensky, A.Y. (2009). Regulatory T-cell suppressor program co-opts transcription factor IRF4 to control T(H)2 responses. Nature 458, 351-356.
Altschul, S. F., Madden, T. L., Schäffer, A. A., Zhang, J., Zhang, Z., Miller, W., & Lipman, D. J. (1997). Gapped BLAST and PSI-BLAST: a new generation of protein database search programs. Nucleic acids research, 25(17), 3389-3402.
Altschul, S. F., Gish, W., Miller, W., Myers, E. W., & Lipman, D. J. (1990). Basic local alignment search tool. Journal of molecular biology, 215(3), 403-410.
Henikoff, S., & Henikoff, J. G. (1992). Amino acid substitution matrices from protein blocks. Proceedings of the National Academy of Sciences, 89(22), 10915-10919.
Karlin, S., & Altschul, S. F. (1993). Applications and statistics for multiple high-scoring segments in molecular sequences. Proceedings of the National Academy of Sciences, 90(12), 5873-5877.

\* cited by examiner

IRF-4 ENGINEERED T CELLS AND USES THEREOF IN TREATING CANCER

CROSS REFERENCE TO RELATED APPLICATIONS

This application is a national stage application filed under 35 U.S.C. § 371 of PCT/US2019/019745 filed Feb. 27, 2019, which claims the benefit of U.S. Provisional Patent Application Ser. No. 62/635,846 filed Feb. 27, 2018, the disclosures of which are expressly incorporated herein by reference.

FIELD

The disclosure generally relates to cancer and cancer therapies, particularly immunotherapies.

BACKGROUND

T cells recognizing tumor-specific antigens can be found in cancer patients, but their function is generally impaired. This functional impairment or "dysfunction" of tumor reactive T cells has recently been documented as a major challenge for developing effective immunotherapies. Currently, the most potent immunotherapies for solid tumors, such as immune checkpoint blockades (e.g., antibodies against PD-1/PD-L1 or CTLA-4), only partially and transiently reverse the "dysfunction" of tumor-reactive T cells, and work in only 20-30% of cancer patients.

T cell dysfunction, such as exhaustion and anergy, represents distinct T cell differentiation states following antigen encounter (Schietinger and Greenberg, 2014). The dysfunctional differentiation of T cells involves the transcriptional induction of essential negative regulators that inhibit T cell function (Fathman and Lineberry, 2007; Wherry and Kurachi, 2015). For instance, dysfunctional T cells that arise during certain chronic infections and cancers sustainably express various inhibitory receptors, including programmed cell death protein 1 (PD-1), CD160, lymphocyte-activation gene 3 (LAG3), B and T lymphocyte attenuator (BTLA), and cytotoxic T lymphocyte antigen 4 (CTLA-4) (Crawford et al., 2014; Schietinger et al., 2016). These receptors exert inhibitory effects on T cell function. Blockade of PD-1, programmed death-ligand 1 (PD-L1), or CTLA-4 has been successfully used to treat several cancer types by reversing T cell dysfunction (Zarour, 2016). Transcription factors T-bet, Blimp-1, NFAT, and FOXO1 regulate PD-1 expression and have been implicated in T cell exhaustion and dysfunction (Wherry and Kurachi, 2015).

Interferon regulatory factor 4 (IRF4) is a member of the IRF family of transcription factors and is preferentially expressed in hematopoietic cells. It plays essential roles in many aspects of T cell, B cell and dendritic cell differentiation and function (Huber and Lohoff, 2014; Ochiai et al., 2013; Vander Lugt et al., 2014). In T cells, IRF4 is promptly expressed within hours following TCR stimulation, and its expression level is TCR affinity dependent (Man et al., 2013). IRF4 controls the differentiation of Th2, Th9, Th17, Tfh, Treg, and cytotoxic effector CD8+ T cells (Bollig et al., 2012; Brustle et al., 2007; Cretney et al., 2011; Huber et al., 2008; Staudt et al., 2010; Yao et al., 2013; Zheng et al., 2009). Irf4-deficient T cells exhibit a severe functional defect in T cell-mediated responses, including microbial infection, allergy, graft-versus-host reaction, and autoimmunity (Brustle et al., 2007; Grusdat et al., 2014; Huber and Lohoff, 2014; Mittrucker et al., 1997; Staudt et al., 2010).

SUMMARY

The disclosed subject matter relates to compositions and methods for increasing IRF4 polypeptide expression in T-cells. The compositions and methods are useful for treating diseases such as cancer in which higher level expression of IRF4 in T-cells would be beneficial. Numerous methods attempt to treat cancer by administration of therapeutics designed to directly target cancerous cells or to elicit desirable anti-cancer immune responses in other cells. It was discovered herein that increased IRF4 expression in T-cells can enhance anti-cancer properties in a cancer subject, and in some embodiments, profoundly so. In some examples, T-cells can be obtained from a cancer patient, be increased for IRF4 expression in vitro, and subsequently be administered to the cancer patient via adoptive cell transfer. Thus, in these examples, the methods can use the patient's own T-cells as a donor pool to increase the percentage of the patient's T-cells which express higher levels of IRF4. The methods can be performed without administration of chemotherapeutics, which often have extensive deleterious side-effects. Alternatively, it was further discovered in certain examples that combination therapies comprising T-cells having increased IRF4 expression and one or more additional anti-cancer therapeutics can have significant beneficial effects. In some examples, combination therapy in subjects having established tumors resulted in undetectable tumors.

In some aspects, provided herein are methods to treat cancer in a subject comprising administering to the subject a therapeutically effective amount of T-cells of the subject having increased IRF4 polypeptide expression compared to a control. In some embodiments, the control comprises an unmodified T-cell of the subject. In some embodiments, the IRF4 polypeptide comprises an amino acid sequence which is at least 80% identical to SEQ ID NO: 1. In some embodiments, the IRF4 polypeptide is encoded by a polynucleotide comprising a nucleic acid sequence which is at least 70% identical to SEQ ID NO: 2. In some embodiments, the IRF4 polypeptide is encoded by a polynucleotide comprising a nucleic acid sequence which is at least 70% identical to SEQ ID NO: 3. In some embodiments, at least about one million T-cells are administered. In some embodiments, the IRF4 polypeptide expression is increased by at least 50% compared to the control. In some embodiments, the T-cells comprise tumor-specific T-cells. In some embodiments, the T-cells comprise CD8+ T-cells. In some embodiments, the administering comprises intratumoral injection. In some embodiments, the method further comprises overexpressing the IRF4 polypeptide in the T-cells. In some embodiments, the overexpressing step comprises introducing into the T-cells a polynucleotide comprising a nucleic acid sequence which is at least 70% identical to SEQ ID NO: 2. In some embodiments, the overexpressing step comprises introducing into the T-cells a polynucleotide comprising a nucleic acid sequence which is at least 70% identical to SEQ ID NO: 3. In some embodiments, the polynucleotide is comprised in a viral vector. In some embodiments, the method further comprises administering one or more additional anti-cancer therapeutics. In some embodiments, the one or more additional anti-cancer therapeutics comprises a T-cell modulator, a cell-cycle regulator, or combinations thereof. In some embodiments, the T-cell modulator comprises a cytokine, for instance IL-2. In some embodiments, the cell-cycle regulator comprises an immune checkpoint blockade, for instance, an anti-PD-L1 antibody, an anti-PD-1 antibody, an anti-CTLA-4 antibody, or combinations thereof. In some embodiments, the one or more additional anti-cancer therapeutics comprises IL-2 and an anti-PD-L1 antibody. In some embodiments, the cancer comprises melanoma, breast cancer, colon cancer, or lymphoma.

Also disclosed herein are methods to predict the likelihood that a subject having cancer will respond therapeutically to a therapy comprising administering to the subject an effective amount of T-cells of the subject having increased IRF4 polypeptide expression compared to a control, the method comprising obtaining T-cells from the recipient; and measuring IRF4 expression in the T-cells; wherein a level of IRF4 expression in the T-cells which is not increased compared to the control indicates the subject has an increased likelihood of responding therapeutically to the therapy.

Also disclosed herein are methods of increasing tumor reactivity of a T-cell comprising increasing IRF4 polypeptide expression in the T-cell, thereby increasing tumor reactivity of the T-cell.

Also disclosed herein are compositions comprising a T-cell comprising a viral vector comprising a polynucleotide encoding an IRF4 polypeptide. In some embodiments, the T-cell comprises a CD8+ T-cell. In some embodiments, the T-cell comprises a chimeric antigen receptor (CAR) T-cell.

Additional aspects and advantages of the disclosure will be set forth, in part, in the detailed description and any claims which follow, and in part will be derived from the detailed description or can be learned by practice of the various aspects of the disclosure. The advantages described below will be realized and attained by means of the elements and combinations particularly pointed out in the appended claims. It is to be understood that both the foregoing general description and the following detailed description are exemplary and explanatory only and are not restrictive of the disclosure.

BRIEF DESCRIPTION OF THE DRAWINGS

The accompanying drawings, which are incorporated in and constitute a part of this specification, illustrate certain examples of the present disclosure and together with the description, serve to explain, without limitation, the principles of the disclosure. Like numbers represent the same element(s) throughout the figures.

(FIG. 5A) The graph shows the tumor growth (mean±SD). (FIG. 5B) The graph shows the survival curves of tumor-bearing mice. *p<0.05; ***p<0.001.

(FIG. 6A) The graph shows the tumor growth (mean±SD). (FIG. 6B) The graph shows the survival curves of tumor-bearing mice.

(FIG. 8A) The graph shows tumor growth (mean±SD). (FIG. 8B) Images show the tumor progression on mice at day 20 after tumor cell injection.

DETAILED DESCRIPTION

Figure 1:
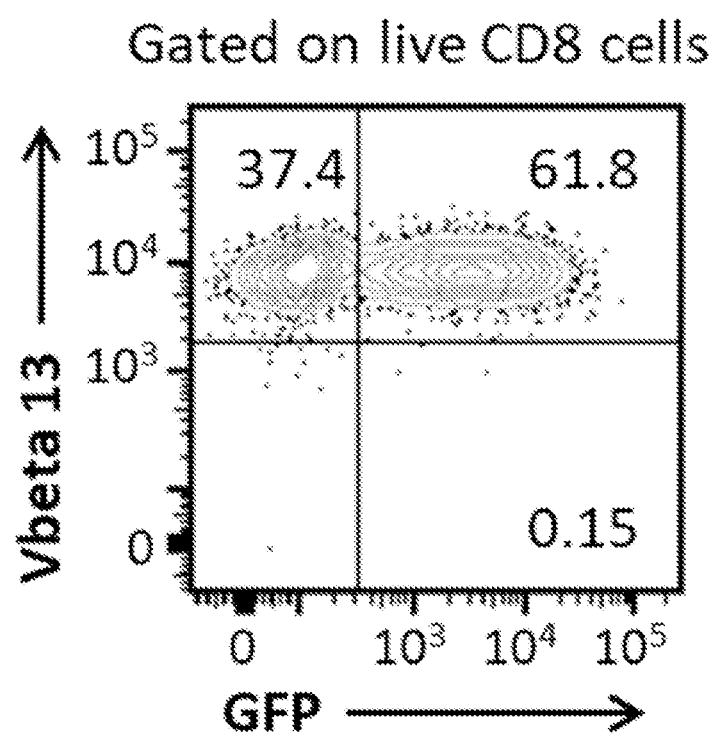
FIG. 1 is a graph depicting transduction efficiency of a IRF4-GFP retroviral vector in tumor reactive T cells.

The following description of the disclosure is provided as an enabling teaching of the disclosure in its best, currently known embodiment(s). To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Terminology

Unless defined otherwise, all technical and scientific terms used herein have the same meaning as commonly understood to one of ordinary skill in the art to which this invention belongs. The following definitions are provided for the full understanding of terms used in this specification.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular cell type is disclosed and discussed and a number of modifications that can be made to the cell type are discussed, specifically contemplated is each and every combination and permutation of the cell type and the modifications that are possible unless specifically indicated to the contrary. Thus, if a class of cell types A, B, and C are disclosed as well as a class of cell types D, E, and F and an example of a combination cell type, or, for example, a combination cell type comprising A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that the compositions disclosed herein have certain functions. Disclosed herein are certain structural requirements for performing the disclosed functions, and it is understood that there are a variety of structures which can perform the same function which are related to the disclosed structures, and that these structures will ultimately achieve the same result.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

As used in the specification and claims, the singular form "a," "an," and "the" include plural references unless the context clearly dictates otherwise. For example, the term "an agent" includes a plurality of agents, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

The terms "about" and "approximately" are defined as being "close to" as understood by one of ordinary skill in the art. In some non-limiting embodiments, the terms are defined to be within 10% of the associated value provided. In some non-limiting embodiments, the terms are defined to be within 5%. In still other non-limiting embodiments, the terms are defined to be within 1%.

Grammatical variations of "administer," "administration," and "administering" to a subject include any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time, overlapping in time, or one following the other. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

"Comprising" is intended to mean that the compositions, methods, etc. include the recited elements, but do not exclude others.

"Identical" or "percent identity," in the context of two or more nucleic acids or polypeptide sequences, refer to two or more sequences or subsequences that are the same or have a specified percentage of amino acid residues or nucleotides that are the same (e.g., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) J. Mol. Biol. 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

A polynucleotide is "operably linked" when it is placed into a functional relationship with another nucleic acid sequence. For example, DNA for an amino-acid presequence or secretory leader is operably linked to DNA encoding a polypeptide if it is expressed as a preprotein that participates in the secretion of the polypeptide; a promoter or enhancer is operably linked to a DNA sequence encoding a polypeptide (also known as a coding sequence) if it affects the transcription of the coding sequence; or a ribosome binding site is operably linked to a coding sequence if it is positioned so as to facilitate translation. Generally, "operably linked" means that the polynucleotide sequences being linked are near each other, and, in the case of a secretory leader, contiguous and in reading phase. However, operably linked polynucleotides (e.g. enhancers and coding sequences) do not have to be contiguous. Linking can be accomplished, for example, by ligation at convenient restriction sites. If such sites do not exist, synthetic oligonucleotide adaptors or linkers can be used in accordance with conventional practice. In some embodiments, a promoter is operably linked with a coding sequence when it is capable of affecting (e.g. modulating relative to the absence of the promoter) the expression of a polypeptide from that coding sequence (e.g., the coding sequence is under the transcriptional control of the promoter).

"Pharmaceutically acceptable" component can refer to a component that is not biologically or otherwise undesirable, e.g., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Polynucleotide" and "oligonucleotide" are used interchangeably, and refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. A polynucleotide is composed of a specific sequence of four nucleotide bases: adenine (A); cytosine (C); guanine (G); thymine (T); and uracil (U) for thymine (T) when the polynucleotide is RNA. Thus, the term "polynucleotide sequence" is the alphabetical representation of a polynucleotide molecule.

"Peptide," "protein," and "polypeptide" are used interchangeably to refer to a natural or synthetic molecule comprising two or more amino acids linked by the carboxyl group of one amino acid to the alpha amino group of another. The amino acids may be natural or synthetic, and can contain chemical modifications such as disulfide bridges, substitution of radioisotopes, phosphorylation, substrate chelation (e.g., chelation of iron or copper atoms), glycosylation, acetylation, formylation, amidation, biotinylation, and a wide range of other modifications. A polypeptide may be attached to other molecules, for instance molecules required for function. Examples of molecules which may be attached to a polypeptide include, without limitation, cofactors, polynucleotides, lipids, metal ions, phosphate, etc. Non-limiting examples of polypeptides include peptide fragments, denatured/unstructured polypeptides, polypeptides having quaternary or aggregated structures, etc. There is expressly no requirement that a polypeptide must contain an intended function; a polypeptide can be functional, non-functional, function for unexpected/unintended purposes, or have unknown function. A polypeptide is comprised of approximately twenty, standard naturally occurring amino acids, although natural and synthetic amino acids which are not members of the standard twenty amino acids may also be used. The standard twenty amino acids include alanine (Ala, A), arginine (Arg, R), asparagine (Asn, N), aspartic acid (Asp, D), cysteine (Cys, C), glutamine (Gln, Q), glutamic acid (Glu, E), glycine (Gly, G), histidine, (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V). The terms "polypeptide sequence" or "amino acid sequence" are an alphabetical representation of a polypeptide molecule.

Conservative substitutions of amino acids in proteins and polypeptides are known in the art. For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the polypeptides provided herein.

Substantial changes in protein function or immunological identity are made by selecting substitutions that are less conservative, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

A "derivative" of a protein or peptide can contain post-translational modifications (such as covalently linked carbohydrate), depending on the necessity of such modifications for the performance of a specific function.

A "variant" refers to a molecule substantially similar in structure and immunoreactivity. Thus, provided that two molecules possess a common immunoactivity and can substitute for each other, they are considered "variants" as that term is used herein even if the composition or secondary, tertiary, or quaternary structure of one of the molecules is not identical to that found in the other, or if the amino acid or nucleotide sequence is not identical. Thus, in one embodiment, a variant refers to a protein whose amino acid sequence is similar to a reference amino acid sequence, but does not have 100% identity with the respective reference sequence. The variant protein has an altered sequence in which one or more of the amino acids in the reference sequence is deleted or substituted, or one or more amino acids are inserted into the sequence of the reference amino acid sequence. As a result of the alterations, the variant protein has an amino acid sequence which is at least 30%, 40%, 50%, 60%, 70%, 75%, 80%, 85%, 90%, or 95% identical to the reference sequence. For example, variant sequences which are at least 95% identical have no more than 5 alterations, i.e. any combination of deletions, insertions or substitutions, per 100 amino acids of the reference sequence. Percent identity is determined by comparing the amino acid sequence of the variant with the reference sequence using any available sequence alignment program. An example includes the MEGALIGN project in the DNA STAR program. Sequences are aligned for identity calculations using the method of the software basic local alignment search tool in the BLAST network service (the National Center for Biotechnology Information, Bethesda, Md.) which employs the method of Altschul, S. F., Gish, W., Miller, W., Myers, E. W. & Lipman, D. J. (1990) J. Mol. Biol. 215, 403-410. Identities are calculated by the Align program (DNAstar, Inc.) In all cases, internal gaps and amino acid insertions in the candidate sequence as aligned are not ignored when making the identity calculation.

"Specifically binds" when referring to a polypeptide (including TCRs and antibodies), refers to a binding reaction which is determinative of the presence of the protein or polypeptide or receptor in a heterogeneous population of proteins and/or other biologics. Thus, under designated conditions (e.g., immunoassay conditions), a specified receptor "specifically binds" to its particular "target" (e.g., a TCR specifically binds to an antigen) when it does not bind in a significant amount to other antigens present in the sample or to other biological components to which the ligand or antibody may come in contact in an organism. Generally, a first molecule (e.g., TCR) that "specifically binds" a second molecule (e.g., antigen) has an affinity constant (Ka) greater than about $10^5$ M$^{-1}$ (e.g., $10^6$ M$^{-1}$, $10^7$ M$^{-1}$, $10^8$ M$^{-1}$, $10^9$ M$^{-1}$, $10^{10}$ M$^{-1}$, $10^{11}$ M$^{-1}$, and $10^{12}$ M$^{-1}$ or more) with that second molecule.

"Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

The terms "treat," "treating," "treatment," and grammatical variations thereof as used herein, include partially or completely delaying, curing, healing, alleviating, relieving, altering, remedying, ameliorating, improving, stabilizing, mitigating, and/or reducing the intensity or frequency of one or more diseases or conditions, symptoms of a disease or condition, or underlying causes of a disease or condition. Treatments according to the invention may be applied prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms.

In some instances, the terms "treat", "treating", "treatment" and grammatical variations thereof, include reducing the size of a tumor or reducing the number of tumors. The terms "treat", "treating", "treatment" and grammatical variations thereof, can also include increasing the overall inflammatory response in a tumor, for example as measured by markers of inflammation such as cytokines, as understood by one of skill in the art. The terms "treat", "treating", "treatment" and grammatical variations thereof, can also include increasing the amount of activated tumor-specific T-cells (e.g., CD8+ T cells) infiltrated in or present in a tumor. Measurements of treatment can be compared with prior treatment(s) of the subject, inclusive of no treatment, or compared with the incidence of such symptom(s) in a general or study population.

Methods to Treat Cancer

The compositions and methods disclosed herein can be used to increase IRF4 polypeptide expression in T-cells. The compositions and methods are useful for instances in which higher level expression of IRF4 in T-cells would be beneficial, for example in treating diseases such as cancer. Cancer cells often exhibit immune evasion capabilities, for example by reducing antigenicity and/or stimulating an immunosuppressive local environment. The methods address needs in the art to increase the amount and effectiveness of anti-cancer and anti-tumor immune system effector cells, particularly T-cells. Activated T-cells such as CD8+ T-cells which highly express IRF4 were found to have increased effectiveness against tumors, including tumors capable of rapid and lethal growth. Thus, the methods can increase the amount and effectiveness of a population of a cancer subject's own T-cells, thereby treating the subject's cancer. The methods are advantageous at least because they enhance a cancer subject's own immune effector cells to counter tumor growth and persistence. Additionally, the methods can avoid or reduce the need for administration of highly toxic chemotherapeutics prone to causing extensive side-effects. Indeed, the methods can reinvigorate the cancer patient's own T-cell populations to function more effectively as anti-tumor cells, thereby enhancing the patient's own anti-cancer defenses. The methods are further advantageous because combination treatment with other anti-cancer immunotherapies can further improve overall outcomes compared to traditional anti-cancer immunotherapies alone.

Disclosed herein is a method to treat cancer in a subject comprising administering to the subject a therapeutically effective amount of T-cells of the subject having increased IRF4 polypeptide expression compared to a control.

Further disclosed herein is a method to treat cancer in a subject comprising administering to the subject a therapeutically effective amount of genetically modified T-cells of the subject, wherein the genetically modified T-cells comprise a heterologous IRF4 polypeptide. Also disclosed is a method to treat cancer in a subject comprising administering to the subject a therapeutically effective amount of genetically modified T-cells of the subject, wherein the genetically modified T-cells comprise increased IRF4 polypeptide expression compared to a control.

The subject can be any mammalian subject, for example a human, dog, cow, horse, mouse, rabbit, etc. which typically has an IRF4 gene. In some embodiments, the subject is a primate, particularly a human. The subject can be a male or female of any age, race, creed, ethnicity, socio-economic status, or other general classifiers.

"IRF4" refers to Interferon Regulatory Factor 4 (IRF4) polypeptide also known as IRF-4 and previously known as MUM1 and LSIRF and, in humans, is encoded by the IRF4 gene. In some embodiments, the IRF4 polypeptide or polynucleotide is that identified in one or more publicly available databases as follows: HGNC: 6119, Entrez Gene: 3662, Ensembl: ENSG00000137265, OMIM: 601900, and UniProtKB: Q15306. The IRF4 polypeptide can be from any vertebrate, particularly from any mammal, for instance livestock such as cows, pigs, and sheep, primates such as humans, gorillas and monkeys, rodents such as mice, rats and guinea pigs, and other mammals such as horse, dog, bear, deer, dolphin, felines, etc. In some embodiments, the IRF4 polypeptide is a human IRF4 polypeptide, or at least a portion of a human IRF4 polypeptide. In some embodiments, the IRF4 polypeptide may be a chimeric polypeptide comprising at least a portion of a human IRF4 polypeptide and a portion of an IRF4 polypeptide from another species or a synthetic source. Example IRF4 polypeptides can include, for example, the following sequences as identified by their accession numbers: Human [*Homo sapiens*] IRF4 isoform 1, NCBI Reference Sequence: NP_002451.2, GI: 167555104; Human IRF4 isoform 2, NCBI Reference Sequence: NP_001182215.1, GI: 305632828; House mouse [*Mus musculus*] IRF4 isoform a, NCBI Reference Sequence: NP_038702.1, GI: 7305519; House mouse IRF4 isoform b, NCBI Reference Sequence: NP_001334437.1, GI: 1109303185; The brown rat [*Rattus norvegicus*] IRF4, NCBI Reference Sequence: NP_001099578.1, GI: 157816963; Chinese hamster [*Cricetulus griseus*] IRF4, GenBank: RLQ69839.1, GI: 1494136450; Sheep [*Ovis aries*] IRF4, NCBI Reference Sequence: XP_027814722.1, GI: 1567534866; Cattle [*Bos taurus*] IRF4, NCBI Reference Sequence: NP_001193091.1, GI: 329663890.

In some embodiments, the IRF4 polypeptide comprises an amino acid sequence which is at least 80% identical to SEQ ID NO: 1. In some embodiments, the IRF4 polypeptide comprises an amino acid sequence which is at least 85%, at least 90%, at least 95%, at least 98%, or at least 99% identical to SEQ ID NO: 1. In some embodiments, the IRF4 polypeptide comprises SEQ ID NO: 1. The IRF4 polypeptide can comprise endogenous IRF4 polypeptide expressed from the chromosome of the T-cell, exogenous IRF4 polypeptide expressed from an exogenously supplied polynucleotide, or combinations thereof.

In some embodiments, the IRF4 polypeptide is encoded by a polynucleotide comprising a nucleic acid sequence which is at least 70% identical to SEQ ID NO: 2, or a variant or fragment thereof. In some embodiments, a polynucleotide encoding the IRF4 polypeptide comprises a nucleic acid sequence which is at least 75%, at least 80%, at least 85%, at least 90%, at least 95%, at least 98%, or at least 99% identical to SEQ ID NO: 2, or a variant or fragment thereof. In some embodiments, a polynucleotide encoding the IRF4 polypeptide comprises SEQ ID NO: 2. In some embodiments, a polynucleotide encoding the IRF4 polypeptide comprises SEQ ID NO: 2, or a variant or fragment thereof. In some embodiments, the IRF4 polypeptide is encoded by a polynucleotide comprising a nucleic acid sequence which is at least 70% identical to SEQ ID NO: 3, or a variant or fragment thereof. In some embodiments, a polynucleotide encoding the IRF4 polypeptide comprises a nucleic acid sequence which is at least 75%, at least 80%, at least 85%, at least 90%, at least 95%, at least 98%, or at least 99% identical to SEQ ID NO: 3, or a variant or fragment thereof. In some embodiments, a polynucleotide encoding the IRF4 polypeptide comprises SEQ ID NO: 3. In some embodiments, a polynucleotide encoding the IRF4 polypeptide comprises SEQ ID NO: 3, or a variant or fragment thereof. The polynucleotide encoding the IRF4 polypeptide can comprise the endogenous polynucleotide comprised within the chromosome of the T-cell, an exogenous polynucleotide encoding an IRF4 polypeptide, or combinations thereof.

In some embodiments, the IRF4 polypeptide comprises an amino acid sequence which is at least 80% identical to SEQ ID NO: 4. In some embodiments, the IRF4 polypeptide comprises an amino acid sequence which is at least 85%, at least 90%, at least 95%, at least 98%, or at least 99% identical to SEQ ID NO: 4. In some embodiments, the IRF4 polypeptide comprises SEQ ID NO: 4. The IRF4 polypeptide can comprise endogenous IRF4 polypeptide expressed from the chromosome of the T-cell, exogenous IRF4 polypeptide expressed from an exogenously supplied polynucleotide, or combinations thereof.

In some embodiments, the IRF4 polypeptide is encoded by a polynucleotide comprising a nucleic acid sequence which is at least 70% identical to SEQ ID NO: 5, or a variant or fragment thereof. In some embodiments, a polynucleotide encoding the IRF4 polypeptide comprises a nucleic acid sequence which is at least 75%, at least 80%, at least 85%, at least 90%, at least 95%, at least 98%, or at least 99% identical to SEQ ID NO: 5, or a variant or fragment thereof. In some embodiments, a polynucleotide encoding the IRF4 polypeptide comprises SEQ ID NO: 5. In some embodiments, a polynucleotide encoding the IRF4 polypeptide comprises SEQ ID NO: 5, or a variant or fragment thereof. In some embodiments, the IRF4 polypeptide is encoded by a polynucleotide comprising a nucleic acid sequence which is at least 70% identical to SEQ ID NO: 6, or a variant or fragment thereof. In some embodiments, a polynucleotide encoding the IRF4 polypeptide comprises a nucleic acid sequence which is at least 75%, at least 80%, at least 85%, at least 90%, at least 95%, at least 98%, or at least 99% identical to SEQ ID NO: 6, or a variant or fragment thereof. In some embodiments, a polynucleotide encoding the IRF4 polypeptide comprises SEQ ID NO: 6. In some embodiments, a polynucleotide encoding the IRF4 polypeptide comprises SEQ ID NO: 6, or a variant or fragment thereof. The polynucleotide encoding the IRF4 polypeptide can comprise the endogenous polynucleotide comprised within the chromosome of the T-cell, an exogenous polynucleotide encoding an IRF4 polypeptide, or combinations thereof. In some embodiments, a polynucleotide encoding the IRF4 polypeptide is recombinant, isolated, or purified.

The T-cells of the subject can be obtained from the subject by any means appropriate to recover at least some live T-cells capable of being increased in IRF4 polypeptide expression. For example, the T-cells can be obtained from a biological sample of the subject. The biological sample can be any T-cell-containing biological sample, for example, blood, plasma, lymph, tissue, tumor biopsy, and the like. The biological sample can be obtained by standard medical, clinical, and/or phlebotomy techniques, and the biological sample can be further processed as required (e.g., purification, culture, storage) in preparation for or in accompaniment with increasing IRF4 polypeptide expression in the T-cells.

An array of T-cell types are compatible with the herein disclosed methods, for example effector T-cells, helper T-cells, cytotoxic T-cells, memory T-cells, regulatory T-cells, gamma-delta T-cells, tumor infiltrating T cells, engineered T cells, chimeric antigen receptor (CAR) T cells etc. In some embodiments, the T-cells comprise CD4+ T-cells, CD8+ T-cells, or combinations thereof. In some embodiments, the T-cells comprise CD8+ T-cells. CD8+ T-cells are also referred to as cytotoxic T-cells and can function to kill specifically recognized cells (e.g., tumor cells). Thus, selection of CD8+ T-cells can, in some embodiments, provide a therapeutically effective amount of T-cells of the subject having increased IRF4 polypeptide expression which are specifically cytotoxic to tumor cells. In some embodiments, the cells are isolated or purified.

Tumor-specific T-cells can be found in subjects having cancer, but function of these T-cells is generally impaired. However, in some embodiments, selection of tumor-specific T-cells can be advantageous, for example to directly administered T-cells to tumors, thereby facilitating increased tumor infiltration. Thus, in some embodiments, the T-cells comprise tumor-specific T-cells of the subject. One biological sample which can serve as a source of tumor-specific T-cells is a tumor biopsy, although tumor-specific T-cells can be found in an array of other biological samples (e.g., as circulating tumor-specific T-cells in the blood). Alternatively, T-cells of the subject which are not tumor-specific can be stimulated with one or more tumor-specific antigens by known methods to induce the T-cells to become tumor-specific T-cells. As used herein, the term "tumor-specific T-cell" refers to a T cell which expresses a T cell antigen receptor (TCR) that specifically recognizes (or binds) an antigen specific for a tumor cell. Generally, a tumor-specific T-cell should not recognize or bind an antigen from a non-tumor cell (e.g., a healthy cell), although the T-cell may have some insignificant binding affinity for a non-tumor cell antigen.

In some or further embodiments, the T-cells are activated T-cells. Activation of T-cells can be achieved in vivo or in vitro, for example by contacting the T-cells with an MHC-bound antigen and a costimulatory agent (e.g., CD80, CD86, etc.). Co-stimulation results in a T-cell in an activated state, which includes intracellular signaling and can result in proliferation, effector function, or death. Activation and expansion can facilitate obtaining a sufficient number of IRF4-engineered T cells. For example and without limitation, methods to activate T cells include stimulation with beads conjugated with anti-CD3 and anti-CD28 antibodies, stimulation with antigen-presenting cells and antigens/peptides, stimulation with antigen-presenting cells and soluble anti-CD3 antibodies, stimulation with cytokines such as IL-2, IL-4, IL-7, and IL-21, and combinations thereof.

Disclosed herein are genetically modified T-cells overexpressing IRF4 polypeptide expression compared to a control. The genetically modified T-cells can include a vector that has integrated into the chromosome, wherein the vector comprises a nucleic acid sequence encoding an IRF4 polypeptide. The genetically modified T-cells can include vector that does not integrate into the chromosome (and is expressed episomally), wherein the vector comprises a nucleic acid sequence encoding an IRF4 polypeptide. As disclosed herein, the T-cells of the subject can have increased IRF4 polypeptide expression compared to a control. The control can comprise a biological sample. Alternatively, a collection of values used as a standard applied to one or more subjects (e.g., a general number or average that is known and not identified in the method using a sample). In some embodiments, the control comprises an unmodified cell of the subject (e.g., a baseline sample). An unmodified cell of the subject can be obtained from the subject prior to the administration step. By "unmodified cell," it is meant that the cell is obtained from a subject, or from a biological sample of a subject, and measured for IRF4 polypeptide expression without additional steps or manipulations performed on the cell beyond those required to obtain the cell and measure IRF4 polypeptide expression. For example, an unmodified cell may be obtained by a standard phlebotomy technique, centrifuged to remove blood or plasma liquid components, washed and resuspended in buffered solutions, and subjected to a polypeptide measurement protocol (e.g., the cell may be lysed, and the contents extracted and subjected to a Western blot analysis using an anti-IRF4 monoclonal antibody). A storage step can be included between the obtaining step and the IRF4 measuring step (e.g., in cryogenic conditions) for both the control and the T-cells to be administered to the subject.

In some embodiments, the control comprises an unmodified T-cell of the subject. In some embodiments, the control comprises an unmodified T-cell of the subject that is the same T-cell type as the T-cells of the subject used in the administration step. For example and without limitation, the control can comprise an unmodified CD8+ T-cell of the subject in embodiments comprising administering CD8+ T-cells of the subject having increased IRF4 polypeptide expression. In some or further embodiments, the control can be a cell from a batch of T-cells obtained from the subject (e.g., from the subject's tumor), wherein the batch of T-cells is partitioned into a first group comprising unmodified T-cell controls and a second group comprising T-cells having increased IRF4 polypeptide expression. However, it is neither required that the control and the administered T-cells be of the same T-cell type, nor that the control and the administered T-cells be obtained from the subject at the same or similar time.

The herein disclosed methods include administering T-cells of the subject having increased IRF4 polypeptide expression. Generally, therapeutic efficacy of the disclosed treatments are proportional to IRF4 polypeptide expression: as IRF4 polypeptide expression increases in the T-cells, so does the therapeutic efficacy of those T-cells. However, the degree of proportionality can vary widely based on an array of factors (e.g., at different levels of IRF4 polypeptide expression, or between subjects), and a maximum therapeutic efficacy can be obtained despite further increases in IRF4 polypeptide expression.

In some embodiments, the administered T-cells have at least 50% increased IRF4 polypeptide expression compared to a control. In some embodiments, the administered T-cells have at least 75%, at least 90%, or at least 99% increased IRF4 polypeptide expression compared to a control. In some embodiments, the administered T-cells have at least two-fold, at least three-fold, at least five-fold, at least ten-fold, at least 25-fold, at least 50-fold, or at least 100-fold increased IRF4 polypeptide expression or more compared to a control.

The administered T-cells of the subject have increased IRF4 polypeptide expression. Expression levels in both the administered T-cells and the control can be measured via a wide array of methods used to measure gene or polypeptide expression levels. In some embodiments, IRF4 polypeptide expression can be measured at the gene transcription level. For example and without limitation, levels of mRNA transcripts can be determined by radiation absorbance (e.g., ultraviolet light absorption at 260, 280, or 230 nm), quantification of fluorescent dye or tag emission (e.g., ethidium bromide intercalation), quantitative polymerase chain reaction (qPCR) of cDNA produced from mRNA transcripts, southern blot analysis, gene expression microarray, or other known methods. Increased levels of mRNA transcripts can be used to infer increased levels of polypeptide expression. In some embodiments, IRF4 polypeptide expression can be measured at the post-translational level. For example and without limitation, levels of polypeptides can be determined by radiation absorbance (e.g., ultraviolet light), bicinchoninic acid (BCA) assay, Bradford assay, biuret test, Lowry method, Coomassie-blue staining, functional or enzymatic assay, immunodetection and/or Western blot analysis, flow cytometric analysis and other suitable methods. In some embodiments, the IRF4 polypeptide expression can be determined by contacting the T cells with an anti-IRF4 antibody (e.g., a monoclonal antibody) and analyzing the binding results by flow cytometric analysis.

IRF4 polypeptide expression can be increased in the T-cells of the subject in a number of ways. Expression of chromosomally-encoded IRF4 (also referred to as native IRF4) can be increased by application of an agent and/or a particular growth condition which induce increased native IRF4 chromosomal expression. For example and without limitation, expression of chromosomally-encoded IRF4 can be increased by TCR stimulation (e.g., via MEK1/2 pathway), co-stimulation (e.g., CD28, OX40, 4-1BB, etc.), or through selective activation of the chromosomally-encoded IRF4 gene with the CRISPR/Cas9 system. In some or further embodiments, IRF4 can be increased by indirect methods, such as increasing activity or function of gene products involved in promoting IRF4 expression, decreasing activity or function of gene products involved in repressing IRF4 expression, or decreasing the rate of IRF4 degradation or inactivation within cells.

Alternatively, or in combination with increased native IRF4 expression, IRF4 polypeptide expression can be increased in the T-cells by introducing a polynucleotide encoding an IRF4 polypeptide (e.g., an exogenous polynucleotide). Thus, the methods can further comprise overexpressing an exogenous IRF4 polypeptide in the T-cells which can have, but need not have, a different amino acid sequence compared to the IRF4 polypeptide encoded by the native, chromosomal IRF4 gene of the T-cells. For example, the chromosomal IRF4 gene can be sequenced and used to synthesize a sequence copy to be ligated or inserted into a polynucleotide to be introduced into the T-cell, thereby resulting in expression of an IRF4 polypeptide identical to that encoded by the native, chromosomal IRF4 gene. Due to redundancy in the genetic code, expression of an IRF4 polypeptide identical to that encoded by the native, chromosomal IRF4 gene can also be achieved by use of a polynucleotide containing a nucleotide sequence which varies from that of the native, chromosomal IRF4 gene but encodes an identical protein. Alternatively, a polynucleotide containing a nucleotide sequence which varies from that of the native, chromosomal IRF4 gene and encodes a different IRF4 protein (e.g., a consensus IRF4 amino acid sequence, or an amino acid sequence which is at least 80% identical to SEQ ID NO: 1 or SEQ ID NO: 4) can be used. The polynucleotide encoding an IRF4 polypeptide is typically operably linked to a promoter, which can be constitutive or inducible.

In some embodiments, the genetically modified T-cells comprise a heterologous polynucleotide comprising a nucleic acid sequence which is at least 70% identical to SEQ ID NO: 2, or a fragment or variant thereof. In some embodiments, the genetically modified T-cells comprise a heterologous polynucleotide comprising a nucleic acid sequence which is at least 75%, at least 80%, at least 85%, at least 90%, at least 95%, at least 98%, or at least 99% identical to SEQ ID NO: 2, or a fragment or variant thereof. In some embodiments, the genetically modified T-cells comprise a heterologous polynucleotide comprising a nucleic acid sequence which is at least 70% identical to SEQ ID NO: 3, or a fragment or variant thereof. In some embodiments, the genetically modified T-cells comprise a heterologous polynucleotide comprising a nucleic acid sequence which is at least 75%, at least 80%, at least 85%, at least 90%, at least 95%, at least 98%, or at least 99% identical to SEQ ID NO: 3, or a fragment or variant thereof. In some embodiments, the genetically modified T-cells comprise a heterologous polynucleotide comprising a nucleic acid sequence which is at least 70% identical to SEQ ID NO: 5, or a fragment or variant thereof. In some embodiments, the genetically modified T-cells comprise a heterologous polynucleotide comprising a nucleic acid sequence which is at least 75%, at least 80%, at least 85%, at least 90%, at least 95%, at least 98%, or at least 99% identical to SEQ ID NO: 5, or a fragment or variant thereof. In some embodiments, the genetically modified T-cells comprise a heterologous polynucleotide comprising a nucleic acid sequence which is at least 70% identical to SEQ ID NO: 6, or a fragment or variant thereof. In some embodiments, the genetically modified T-cells comprise a heterologous polynucleotide comprising a nucleic acid sequence which is at least 75%, at least 80%, at least 85%, at least 90%, at least 95%, at least 98%, or at least 99% identical to SEQ ID NO: 6, or a fragment or variant thereof. As used herein, a polynucleotide sequence is "heterologous" (or sometimes referred to as "exogenous") to a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from naturally occurring allelic variants. In some embodiments, the overexpressing step comprises introducing into the T-cells a polynucleotide comprising a nucleic acid sequence which is at least 70% identical to SEQ ID NO: 2, or a fragment or variant thereof. In some embodiments, the overexpressing step comprises introducing into the T-cells a polynucleotide comprising a nucleic acid sequence which is at least 75%, at least 80%, at least 85%, at least 90%, at least 95%, at least 98%, or at least 99% identical to SEQ ID NO: 2, or a fragment or variant thereof. In some embodiments, the overexpressing step comprises introducing into the T-cells a polynucleotide comprising a nucleic acid sequence which comprises SEQ ID NO: 2, or a fragment or variant thereof. In some embodiments, the overexpressing step comprises introducing into the T-cells a polynucleotide comprising a nucleic acid sequence which is at least 70% identical to SEQ ID NO: 3, or a fragment or variant thereof. In some embodiments, the overexpressing step comprises introducing into the T-cells a polynucleotide comprising a nucleic acid sequence which is at least 75%, at least 80%, at least 85%, at least 90%, at least 95%, at least 98%, or at least 99% identical to SEQ ID NO: 3, or a fragment or variant thereof. In some embodiments, the overexpressing step comprises introducing into the T-cells a polynucleotide comprising a nucleic acid sequence which comprises SEQ ID NO: 3, or a fragment or variant thereof. In some embodiments, the overexpressing step comprises introducing into the T-cells a polynucleotide comprising a nucleic acid sequence which is at least 70% identical to SEQ ID NO: 5, or a fragment or variant thereof. In some embodiments, the overexpressing step comprises introducing into the T-cells a polynucleotide comprising a nucleic acid sequence which is at least 75%, at least 80%, at least 85%, at least 90%, at least 95%, at least 98%, or at least 99% identical to SEQ ID NO: 5, or a fragment or variant thereof. In some embodiments, the overexpressing step comprises introducing into the T-cells a polynucleotide comprising a nucleic acid sequence which comprises SEQ ID NO: 5, or a fragment or variant thereof. In some embodiments, the overexpressing step comprises introducing into the T-cells a polynucleotide comprising a nucleic acid sequence which is at least 70% identical to SEQ ID NO: 6, or a fragment or variant thereof. In some embodiments, the overexpressing step comprises introducing into the T-cells a polynucleotide comprising a nucleic acid sequence which is at least 75%, at least 80%, at least 85%, at least 90%, at least 95%, at least 98%, or at least 99% identical to SEQ ID NO: 6, or a fragment or variant thereof. In some embodiments, the overexpressing step comprises introducing into the T-cells a polynucleotide comprising a nucleic acid sequence which comprises SEQ ID NO: 6, or a fragment or variant thereof. The polynucleotide can comprise RNA (e.g., mRNA), DNA (e.g., with or without introns), or cDNA.

As used herein, the term "introducing," "introduce," and grammatical variations thereof, as it relates to introducing a polynucleotide into T-cells, refers to any method suitable for transferring the polynucleotide into the cell. The term includes as examples, but is not limited to, conjugation, transformation/transfection (e.g., divalent cation exposure, heat shock, electroporation), nuclear microinjection, incubation with calcium phosphate polynucleotide precipitate, high velocity bombardment with polynucleotide-coated microprojectiles (e.g., via gene gun), lipofection, cationic polymer complexation (e.g., DEAE-dextran, polyethylenimine), dendrimer complexation, mechanical deformation of cell membranes (e.g., cell-squeezing), sonoporation, optical transfection, impalefection, hydrodynamic polynucleotide delivery, *Agrobacterium*-mediated transformation, transduction (e.g., transduction with a virus or viral vector), natural or artificial competence, protoplast fusion, magnetofection, nucleofection, or combinations thereof. An introduced polynucleotide can be genetically integrated or exist extrachromosomally. As used herein, the term "integrated" used in reference to a polynucleotide means the polynucleotide is incorporated (physically inserted) into the chromosomal DNA of a host cell.

In some embodiments, the polynucleotide encoding IRF4 polypeptide is a naked DNA or is comprised in a nanoparticle (e.g., liposomal vesicle, porous silicon nanoparticle, gold-DNA conjugate particle, polyethylenimine polymer particle, cationic peptides, etc.). In some embodiments, the polynucleotide encoding IRF4 polypeptide is comprised in a plasmid or in a virus or viral vector. As used herein, the terms "virus" and "viral vector" are used interchangeably and refer to a virus or virus-like particle containing genetic material which can be introduced into a eukaryotic cell. Thus, in some embodiments, a virus comprising a polynucleotide encoding IRF4 polypeptide can be transduced into the T-cells of the subject. The type of virus or viral vector used for transduction is limited only by compatibility (e.g., low toxicity, capability to enter cells) with living T-cells and should not result in significant adverse effects on the subject when introduced into T-cells administered to the subject. Suitable viruses and viral vectors include adenovirus, lentivirus, retrovirus, among others.

Increased IRF4 expression should persist for at least a time sufficient for the administered T-cells to result in a therapeutic effect. The IRF4 polypeptide expression levels can be increased before, after, or both before and after administering the T-cells. In embodiments using an inducible promoter to drive expression of an introduced polynucleotide encoding an IRF4 polypeptide, the promoter should be induced (before, after, or both before and after administering the T-cells) to a level or for a time to result in a therapeutic effect. In some embodiments, the IRF4 polypeptide is constitutively expressed at an increased level in the administered T-cells.

The administering step can include any method of introducing the T-cells having increased IRF4 polypeptide expression into the subject appropriate for the T-cell formulation. Administration of a therapeutic amount of cells into a subject is often referred to as adoptive transfer or adoptive cell transfer. Prior to administration, cells for adoptive transfer are typically purified or separated from other cells, for example by fluorescence activated cell sorting (FACS) or microfluidics methods. Cells can be further increased in number (e.g., via culturing) to obtain a sufficient amount of cells for adoptive transfer. The T-cells can be administered in a number of ways, for instance, as circulating T-cells (e.g., by intravenous injection) or implanted into a tissue. In some embodiments, the administering step comprises local administration, for example locally administered near a tumor. In some embodiments, the administering comprises intratumoral injection.

The administering step can include at least one, at least two, at least three, at least four, at least five, at least six, at least seven, at least eight, at least nine, or at least ten dosages. The administering step can be performed before the subject exhibits disease symptoms (e.g., prophylactically), or during or after disease symptoms occur.

In some embodiments, a subsequent administration is provided at least one day after a prior administration, or at least two days, at least three days, at least four days, at least five days, or at least six days after a prior administration. In some embodiments, a subsequent administration is provided at least one week after a prior administration, or at least two weeks, at least three weeks, or at least four weeks after a prior administration. In some embodiments, a subsequent administration is provided at least one month, at least two months, at least three months, at least six months, or at least twelve months after a prior administration.

The amount of T-cells administered to the subject can vary widely, but should be sufficient for the administered T-cells to result in a therapeutic effect. In some embodiments, at least about 1,000 T-cells are administered. In some embodiments, at least about 10,000, at least about 100,000, at least about 500,000, at least about 1,000,000, at least about 5,000,000, at least about 10,000,000, at least about 50,000,000, or at least about 100,000,000 or more T-cells are administered.

Alternatively, the amount of T-cells administered to the subject can be expressed in terms of a dosage amount per body weight. The amount of the disclosed compositions administered to a subject will vary from subject to subject, depending on the nature of the disclosed compositions and/or formulations, the species, gender, age, weight and general condition of the subject, the mode of administration, and the like. Effective dosages and schedules for administering the compositions may be determined empirically, and making such determinations is within the skill in the art. The dosage ranges for the administration of the disclosed compositions are those large enough to produce the desired effect (e.g., to reduce tumor size). The dosage should not be so large as to outweigh benefits by causing adverse side effects, such as unwanted cross-reactions, anaphylactic reactions, and the like. The dosage can be adjusted by the individual clinician in the event of any counterindications. Generally, the disclosed compositions and/or formulations are administered to the subject at a dosage of active component(s) ranging from 0.1 µg/kg body weight to 100 g/kg body weight. In some embodiments, the disclosed compositions and/or formulations are administered to the subject at a dosage of active component(s) ranging from 1 µg/kg to 10 g/kg, from 10 µg/kg to 1 g/kg, from 10 µg/kg to 500 mg/kg, from 10 µg/kg to 100 mg/kg, from 10 µg/kg to 10 mg/kg, from 10 µg/kg to 1 mg/kg, from 10 µg/kg to 500 µg/kg, or from 10 µg/kg to 100 µg/kg body weight. Dosages above or below the range cited above may be administered to the individual subject if desired.

The methods can be performed with or without administration of additional agents (e.g., therapeutic agents, diagnostic agents). In some embodiments, the methods can include administering one or more additional anti-cancer therapeutics in addition to administering a therapeutically effective amount of T-cells having increased IRF4 polypeptide expression. It is understood that methods can encompass any known anti-cancer therapeutic, the specific class of which are not particularly limited. Non-limiting examples of suitable anti-cancer therapeutics which can be used in the methods include Abemaciclib, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride) and other DNA intercalators, Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), altretamine, Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin Chlorambucil), Amifostine, Aminolevulinic Acid, Anastrozole, antiangiogenic agents such as angiostatin, antiestrogens such as tamoxifen, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar, (Irinotecan Hydrochloride), Capecitabine, CAPDX, Carac (Fluorouracil—Topical) and other antimetabolites, Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Ethyol (Amifostine), Etopophos (Etoposide Phosphate), Etoposide and other topoisomerase inhibitors (e.g., camptothecin), Etoposide Phosphate, Evacet (Doxorubicin Hydrochloride Liposome), Everolimus, Evista, (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil—Topical), Fluorouracil Injection, Fluorouracil—Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide and other alkylating agents, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and, Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel) and other mitotic inhibitors, Taxotere (Docetaxel), Tecentriq, (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil—Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and/or Zytiga (Abiraterone Acetate), busulphan, calcium folinate, vindesine, crisantaspase, gefitinib (IRES SA), hydroxyurea, pentostatin, raltitrexed, streptozocin, tegafururacil, tioguanine/thioguanine, treosulfan, vinorelbine, and combinations thereof.

In some embodiments, the one or more additional anti-cancer therapeutics comprises a T-cell modulator. Numerous therapeutic compounds can modulate T-cell responses, activities, growth or proliferation, functions, etc. In some embodiments, the T-cell modulator comprises a soluble compound released by a cell (e.g., steroid, protein, lipid). In some embodiments, the T-cell modulator comprises a cytokine, for example a chemokine, interferon (IFN), interleukin (IL), lymphokine, tumor necrosis factor (TNF), or combinations thereof. In some embodiments, the T-cell modulator comprises IL-4, IL-6, IL-2, IL-12, IL-15, IL-21, IFNα/β, IFNγ, TNFα, or combinations thereof. In some embodiments, the T-cell modulator comprises IL-2.

In some embodiments, the one or more additional anti-cancer therapeutics comprises a cell-cycle regulator such as inhibitors of cyclin-dependent kinases (anti-cdks), an immune checkpoint blockade (also known as a checkpoint inhibitor), or telomerase inhibitors. In some embodiments, the cell-cycle regulator comprises a checkpoint inhibitor selected from anti-PD-L1 antibody (atezolizumab, avelumab, durvalumab), an anti-PD-1 antibody (e.g., pembrolizumab, nivolumab), an anti-CTLA-4 antibody (e.g., Ipilimumab), or combinations thereof. In some embodiments, the one or more additional anti-cancer therapeutics comprises IL-2 and an anti-PD-L1 antibody.

It was surprising that adoptively transferred T-cells comprising increased IRF4 polypeptide expression could alone improve cancer or tumor outcomes. However, the inclusion of one or more additional anti-cancer therapeutics can, in some embodiments, further enhance the anti-tumor effects of the T-cells. For example and without limitation, an example method comprising administering T-cells having increased IRF4 polypeptide expression, anti-PD-L1 antibody, and IL-2 can result, in some embodiments, in clinically undetectable tumors and/or increased survival.

The cancer types for which the methods are useful are not particularly limited. In part because the methods can enhance the subject's own anti-cancer immune effector cells rather than rely on very specific attributes of particular cancer types, the methods are useful for an array of cancers. Non-limiting examples of cancers include Acute granulocytic leukemia, Acute lymphocytic leukemia, Acute myelogenous leukemia (AML), Adenocarcinoma, Adenosarcoma, Adrenal cancer, Adrenocortical carcinoma, Anal cancer, Anaplastic astrocytoma, Angiosarcoma, Appendix cancer, Astrocytoma, Basal cell carcinoma, B-Cell lymphoma, Bile duct cancer, Bladder cancer, Bone cancer Bone marrow cancer, Bowel cancer, Brain cancer, Brain stem glioma, Brain tumor, Breast cancer, Carcinoid tumors, Cervical cancer, Cholangiocarcinoma, Chondrosarcoma, Chronic lymphocytic leukemia (CLL), Chronic myelogenous leukemia (CML), Colon cancer, Colorectal cancer, Craniopharyngioma, Cutaneous lymphoma, Cutaneous melanoma, Diffuse astrocytoma, Ductal carcinoma in situ (DCIS), Endometrial cancer, Ependymoma, Epithelioid sarcoma, Esophageal cancer, Ewing sarcoma, Extrahepatic bile duct cancer, Eye cancer, Fallopian tube cancer, Fibrosarcoma, Gallbladder cancer, Gastric cancer, Gastrointestinal cancer, Gastrointestinal carcinoid cancer, Gastrointestinal stromal tumors (GIST), Germ cell tumor, Gestational Trophoblastic Disease (GTD), Glioblastoma multiforme (GBM), Glioma, Hairy cell leukemia, Head and neck cancer, Hemangioendothelioma, Hodgkin's lymphoma, Hypopharyngeal cancer, Infiltrating ductal carcinoma (IDC), Infiltrating lobular carcinoma (ILC), Inflammatory breast cancer (IBC), Intestinal Cancer, Intrahepatic bile duct cancer, Invasive/infiltrating breast cancer, Islet cell cancer, Jaw/oral cancer, Kaposi sarcoma, Kidney cancer, Laryngeal cancer, Leiomyosarcoma, Leptomeningeal metastases, Leukemia, Lip cancer, Liposarcoma, Liver cancer, Lobular carcinoma in situ, Low-grade astrocytoma, Lung cancer, Lymph node cancer, Lymphoma, Male breast cancer, Medullary carcinoma, Medulloblastoma, Melanoma, Meningioma, Merkel cell carcinoma, Mesenchymal chondrosarcoma, Mesenchymous, Mesothelioma, Metastatic breast cancer, Metastatic melanoma, Metastatic squamous neck cancer, Mixed gliomas, Mouth cancer, Mucinous carcinoma, Mucosal melanoma, Multiple myeloma, Mycosis Fungoides, Myelodysplastic Syndrome, Nasal cavity cancer, Nasopharyngeal cancer, Neck cancer, Neuroblastoma, Neuroendocrine tumors (NETs), Non-Hodgkin's lymphoma, Non-small cell lung cancer (NSCLC), Oat cell cancer, Ocular cancer, Ocular melanoma, Oligodendroglioma, Oral cancer, Oral cavity cancer, Oropharyngeal cancer, Osteogenic sarcoma, Osteosarcoma, Ovarian cancer, Ovarian epithelial cancer, Ovarian germ cell tumor, Ovarian primary peritoneal carcinoma, Ovarian sex cord stromal tumor, Paget's disease, Pancreatic cancer, Papillary carcinoma, Paranasal sinus cancer, Parathyroid cancer, Pelvic cancer, Penile cancer, Peripheral nerve cancer, Peritoneal cancer, Pharyngeal cancer, Pheochromocytoma, Pilocytic astrocytoma, Pineal region tumor, Pineoblastoma, Pituitary gland cancer, Primary central nervous system (CNS) lymphoma, Prostate cancer, Rectal cancer, Renal cell carcinoma, Renal pelvis cancer, Rhabdomyosarcoma, Salivary gland cancer, Sarcoma, Sinus cancer, Skin cancer, Small cell lung cancer (SCLC), Small intestine cancer, Soft tissue sarcoma, Spinal cancer, Spinal column cancer, Spinal cord cancer, Spinal tumor, Squamous cell carcinoma, Stomach cancer, Synovial sarcoma, T-cell lymphoma, Testicular cancer, Throat cancer, Thymoma/thymic carcinoma, Thyroid cancer, Tongue cancer, Tonsil cancer, Transitional cell cancer, Transitional cell cancer, Triple-negative breast cancer, Tubal cancer, Tubular carcinoma, Ureteral cancer, Urethral cancer, Uterine adenocarcinoma, Uterine cancer, Uterine sarcoma, Vaginal cancer, Vulvar cancer, Wilms tumor, Waldenstrom macroglobulinemia, etc., and combinations thereof. In some embodiments, the cancer comprises a solid tumor. In some embodiments, the cancer comprises melanoma, breast cancer, colon cancer, or lymphoma. In some embodiments, the cancer comprises lung cancer or kidney cancer. In some embodiments, the cancer is melanoma. In some embodiments, the cancer is breast cancer. In some embodiments, the cancer is colon cancer. In some embodiments, the cancer is lymphoma.

The methods can include administering T-cells of the subject formulated with a pharmaceutically acceptable carrier and/or as a medicament. Suitable carriers include, but are not limited to, salts, diluents, binders, fillers, solubilizers, disintegrants, preservatives, sorbents, and other components.

Methods to Predict Therapeutic Responsiveness

Also disclosed herein is a method to predict the likelihood that a subject having cancer will respond therapeutically to a therapy comprising administering to the subject an effective amount of T-cells of the subject having increased IRF4 polypeptide expression compared to a control, the method comprising obtaining T-cells from the recipient; and measuring IRF4 expression in the T-cells; wherein a level of IRF4 expression in the T-cells which is not increased compared to the control indicates the subject has an increased likelihood of responding therapeutically to the therapy.

The subject can be any herein disclosed subject, the control can be any herein disclosed control, and the T-cells can be any herein disclosed T-cells having increased IRF4 polypeptide expression. Similarly, the IRF4 polypeptide can be any herein disclosed IRF4 polypeptide, and IRF4 expression can be measured by any herein disclosed method to measure expression levels. Further, the cancer can be any herein disclosed cancer which can respond therapeutically to a therapy comprising administering to the subject an effective amount of T-cells of the subject having increased IRF4 polypeptide expression compared to a control.

In some embodiments, wherein a level of IRF4 expression in the T-cells which is increased compared to the control, such a result indicates the subject does not have an increased likelihood of responding therapeutically to the therapy. However, a subject which does not have an increased likelihood of responding therapeutically to the therapy may nonetheless respond therapeutically to the therapy.

In some embodiments, wherein a level of IRF4 expression in the T-cells which is not increased compared to the control, the method further comprises advising the subject that the subject has an increased likelihood of responding therapeutically to the therapy. In some embodiments, wherein a level of IRF4 expression in the T-cells which is increased compared to the control, the method further comprises advising the subject that the subject does not have an increased likelihood of responding therapeutically to the therapy.

In some embodiments, wherein a level of IRF4 expression in the T-cells which is not increased compared to the control, the method further comprises administering to the subject an effective amount of T-cells of the subject having increased IRF4 polypeptide expression compared to a control. In some such embodiments, the method further comprises administering any one or more herein disclosed additional anti-cancer therapeutics. In some embodiments, the one or more additional anti-cancer therapeutics comprise a T-cell modulator (e.g., IL-2), a cell-cycle regulator (e.g., anti-PD-L1 antibody), or combinations thereof.

As used herein, the term "not increased" as it relates to IRF expression levels refers to a level of IRF4 expression which is not sufficiently increased compared to a control to result in a beneficial therapeutic effect. Thus, in addition to encompassing embodiments in which IRF4 expression is quantitatively lower or unchanged compared to a control, the term also encompasses embodiments in which IRF4 expression is quantitatively higher than a control, but to a degree insufficient to result in a beneficial therapeutic effect. In some embodiments, the term encompasses embodiments in which IRF4 expression is quantitatively but not statistically significantly higher than a control. In some embodiments, the term encompasses embodiments in which IRF4 expression is increased by less than 50% compared to a control. In some embodiments, the term encompasses embodiments in which IRF4 expression is increased by less than 40%, less than 30%, less than 20%, or less than 10% compared to a control.

As used herein, an "effective amount" refers to a sufficient amount of T-cells typically required to provide a desired effect, for example a desired therapeutic effect. The term is intended to encompass amounts of T-cells that typically provide a therapeutic effect (for example, in an average of subjects), but may or may not provide a therapeutic effect in a given subject. As such, a method to predict the likelihood that a subject having cancer will respond therapeutically to a therapy comprising administering to the subject an effective amount of T-cells encompasses amounts of T-cells which are both therapeutic to a given subject and typically sufficient to provide a therapeutic effect (e.g., in an average of subjects), as well as situations in which the T-cells are typically sufficient to provide a therapeutic effect but are not therapeutic for a given subject.

Methods to Increase Tumor Reactivity

Also disclosed herein is a method of increasing tumor reactivity of a T-cell comprising increasing IRF4 polypeptide expression in the T-cell, thereby increasing tumor reactivity of the T-cell. A T-cell is increased for "tumor reactivity" if the T-cell has one or more increased immunological responses to the tumor. For example, a T-cell having increased tumor reactivity can be increased for anti-tumor cytokine signaling and/or release, release of cytotoxic factors (e.g., performs, granzymes, granulysins), proliferation, activation, generation of memory, or other immunological functions.

The T-cells can be any herein disclosed T-cells having increased IRF4 polypeptide expression. Similarly, the IRF4 polypeptide can be any herein disclosed IRF4 polypeptide, and IRF4 expression can be measured by any herein disclosed method to measure expression levels. In some embodiments, the T-cell comprises a tumor-specific CD8+ T-cell.

Compositions

It is understood that the T-cells of the present disclosure can be used in combination with the various compositions, methods, products, and applications disclosed herein.

Despite extensive research into and development of new anti-cancer therapeutics, very few result in FDA-approval and commercial use. Fewer still are additionally indicated for use in a wide array of cancer types. The compositions disclosed herein addresses needs in the art by providing for new compositions which can be used for treating numerous cancer types via novel methods.

Disclosed herein are compositions comprising a T-cell comprising a viral vector comprising a polynucleotide encoding an IRF4 polypeptide. In some embodiments, the IRF4 polypeptide is expressed in the T-cell at an increased level compared to a control.

The IRF4 polypeptide can be any herein disclosed IRF4 polypeptide, and IRF4 expression can be measured by any herein disclosed method to measure expression levels. Similarly, the control can be any herein disclosed control.

Similarly, the viral vector can be any herein disclosed viral vector capable of comprising a polynucleotide encoding an IRF4 polypeptide. By "a T-cell comprising a viral vector," it is meant that at least a portion of the viral vector is located within the confines of the cell membrane of the T-cell; that is, at least a portion of the viral vector is located inside the T-cell. As would be understood by one of skill in the art, the life cycle of many viruses includes the shedding of some biological components upon entry into a host cell. For example, envelop lipids, capsule proteins, and/or attachment proteins can be lost or integrated into the host cell membrane when a virus or viral vector enters a host cell. Therefore, it is understood that the portion of the viral vector located inside the T-cell comprises at least the genetic payload of the viral vector, which comprises the polynucleotide encoding an IRF4 polypeptide. However, every component of the entire virus or viral vector need not be comprised within the interior of the T-cell.

In some embodiments, the polynucleotide comprises a nucleic acid sequence which is at least 70% identical to SEQ ID NO: 2. In some embodiments, the polynucleotide comprises a nucleic acid sequence which is at least 75%, at least 80%, at least 85%, at least 90%, at least 95%, at least 98%, or at least 99% identical to SEQ ID NO: 2. In some embodiments, a polynucleotide comprises SEQ ID NO: 2. In some embodiments, the polynucleotide comprises a nucleic acid sequence which is at least 70% identical to SEQ ID NO: 5. In some embodiments, the polynucleotide comprises a nucleic acid sequence which is at least 75%, at least 80%, at least 85%, at least 90%, at least 95%, at least 98%, or at least 99% identical to SEQ ID NO: 5. In some embodiments, a polynucleotide comprises SEQ ID NO: 5. In some embodiments, the polynucleotide comprises a nucleic acid sequence which is at least 70% identical to SEQ ID NO: 3. In some embodiments, the polynucleotide comprises a nucleic acid sequence which is at least 75%, at least 80%, at least 85%, at least 90%, at least 95%, at least 98%, or at least 99% identical to SEQ ID NO: 3. In some embodiments, a polynucleotide comprises SEQ ID NO: 3. In some embodiments, the polynucleotide comprises a nucleic acid sequence which is at least 70% identical to SEQ ID NO: 6. In some embodiments, the polynucleotide comprises a nucleic acid sequence which is at least 75%, at least 80%, at least 85%, at least 90%, at least 95%, at least 98%, or at least 99% identical to SEQ ID NO: 6. In some embodiments, a polynucleotide comprises SEQ ID NO: 6.

The T-cells can be any herein disclosed T-cells capable of having increased IRF4 polypeptide expression. In some embodiments, the T-cell comprises a CD8+ T-cell. In some embodiments, the T-cell comprises a tumor-specific CD8+ T-cell. In some embodiments, the T-cell is from a human subject. In some embodiments, the T-cell is chimeric antigen receptor (CAR) T-cell.

The compositions can comprise the herein disclosed T-cells and a pharmaceutically acceptable carrier. Also disclosed is a medicament comprising a therapeutically effective amount of T-cells having increased IRF4 polypeptide expression compared to a control.

EXAMPLES

To further illustrate the principles of the present disclosure, the following examples are put forth so as to provide those of ordinary skill in the art with a complete disclosure and description of how the compositions, articles, and methods claimed herein are made and evaluated. They are intended to be purely exemplary of the invention and are not intended to limit the scope of what the inventors regard as their disclosure. These examples are not intended to exclude equivalents and variations of the present invention which are apparent to one skilled in the art. Unless indicated otherwise, temperature is ° C. or is at ambient temperature, and pressure is at or near atmospheric. There are numerous variations and combinations of process conditions that can be used to optimize product quality and performance. Only reasonable and routine experimentation will be required to optimize such process conditions.

Example 1. Transduction Efficiency of a IRF4-GFP Retroviral Vector in Tumor Reactive T Cells The outgrowth of cancer in patients represents the failure of natural cancer-specific immune responses in preventing cancer progression. Adoptive cancer immunotherapy is a promising approach for cancer treatment, and the modern genetic toolbox enables the adoptive transfer of engineered T cells to reprogram or enhance the anticancer immune responses. This example describes the engineering of T-cells having increased IRF4 polypeptide expression, which can be used, in some embodiments, to enhance an anticancer immune response.

A retroviral vector containing an IRF4-GFP gene fusion was produced via the following protocol. The IRF4-GFP gene fusion is expressed primarily as a single transcript, but results in translation of separate IRF4 and GFP proteins due to an internal ribosome entry site (IRES). cDNA fragments encoding mouse Irf4 were amplified by PCR and then cloned into a pMYs-IRES-EGFP retroviral vector (Cell Biolabs). Retroviral particles were produced by transfecting plat-E cells with those retroviral vectors according to the manufacturer's recommendations (Cell Biolabs).

Pmel-1 mice have melanoma-reactive CD8+ T cells that are specific to H2-$D^b$-restricted nonmutated-self/tumor-antigen gp100$_{25-33}$. Melanoma-reactive pmel-1 CD8+ T cells were activated by stimulating splenocytes obtained from pmel-1 mice with 1 μM hgp100$_{25-33}$ peptide for 24 hours.

IRF4-GFP or GFP-control vectors were transduced in pmel-1 cells via the following protocol. After 24-hour activation, pmel-1 splenocytes were incubated with retroviral particles by centrifugation for 2 hours at 780×g and 32° C. in the presence of 8 μg/ml polybrene (Sigma-Aldrich). After centrifugation, cells were cultured for 6 hours at 32° C., and subsequently cultured for additional 16 hours in complete RPMI 1640 medium at 37° C. prior to flow cytometry analysis and in vivo transfer.

Flow cytometry analysis of transduction efficacy was performed via the following: Cultured T cells were stained and analyzed on a LSR II flow cytometer (Beckton Dickinson). A contour plot was gated on the live CD8+ population and shows expression of GFP versus the TCR beta chain (Vβ13) of pmel-1 T cells (FIG. 1). Numbers in the contour plot display the cell percentages in each gate. Almost all live CD8+ T cells in the cultures are Vβ13+ pmel-1 T cells, and more than 60% pmel-1 T cells were successfully transduced with the IRF4-GFP retroviral vector, as indicated by GFP expression. T cells transduced with the IRF4-GFP retroviral vector are occasionally referred to herein as "IRF4-engineered T cells."

Figure 2:
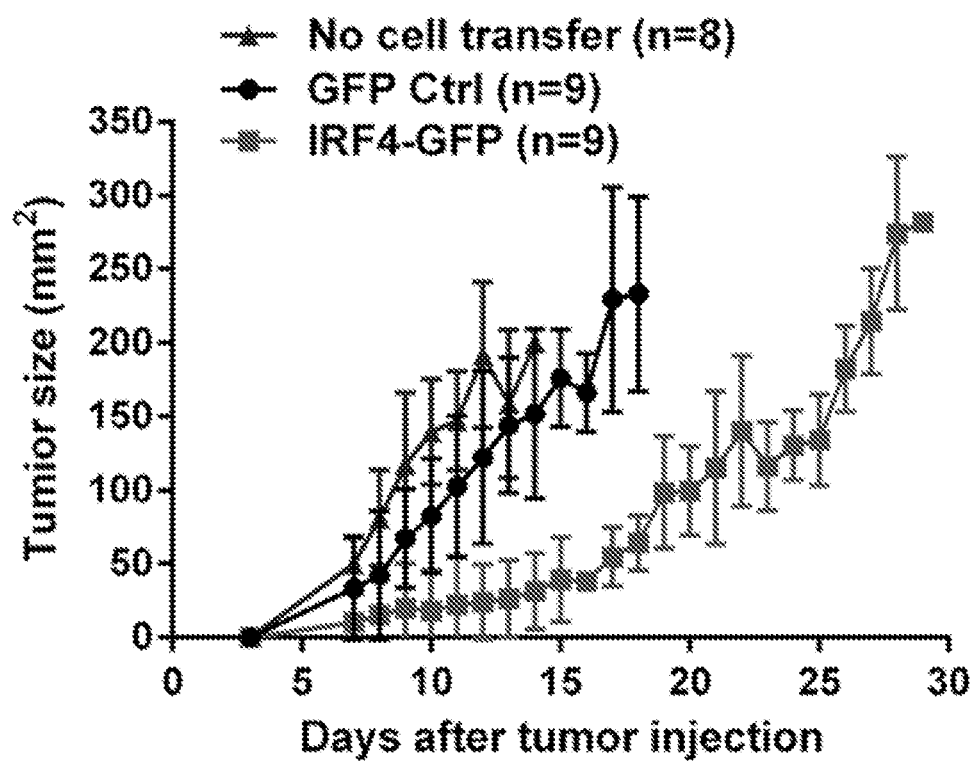
FIG. 2 is a graph depicting reduced cancer progression after in vivo administration of IRF4-engineered T cells.

Example 2. IRF4-Engineered T Cells Suppress Cancer Progression In Vivo 10-week-old C57BL/6J male mice were subcutaneously (s.c.) injected with 5×10$^5$ B16-F10 melanoma cells. On day 3, mice were intravenously (i.v.) injected with cultured pmel-1 splenocytes containing 1×10$^6$ GFP-control (GFP Ctrl group; n=9) or IRF4-GFP (n=9) transduced pmel-1 CD8+ T cells, or were not injected with cells (No cell transfer group; n=8). The GFP-control splenocytes contained a pMYs-IRES-EGFP retroviral vector which did not include IRF4, and therefore express EGFP but not IRF4. Tumor growth (mean±SD) was measured over time for each group (FIG. 2). Results showed that adoptive transfer of melanoma-specific CD8+ T cells reduced the growth rate of tumors in mice. Results are representative of four similar experiments.

Figure 3:
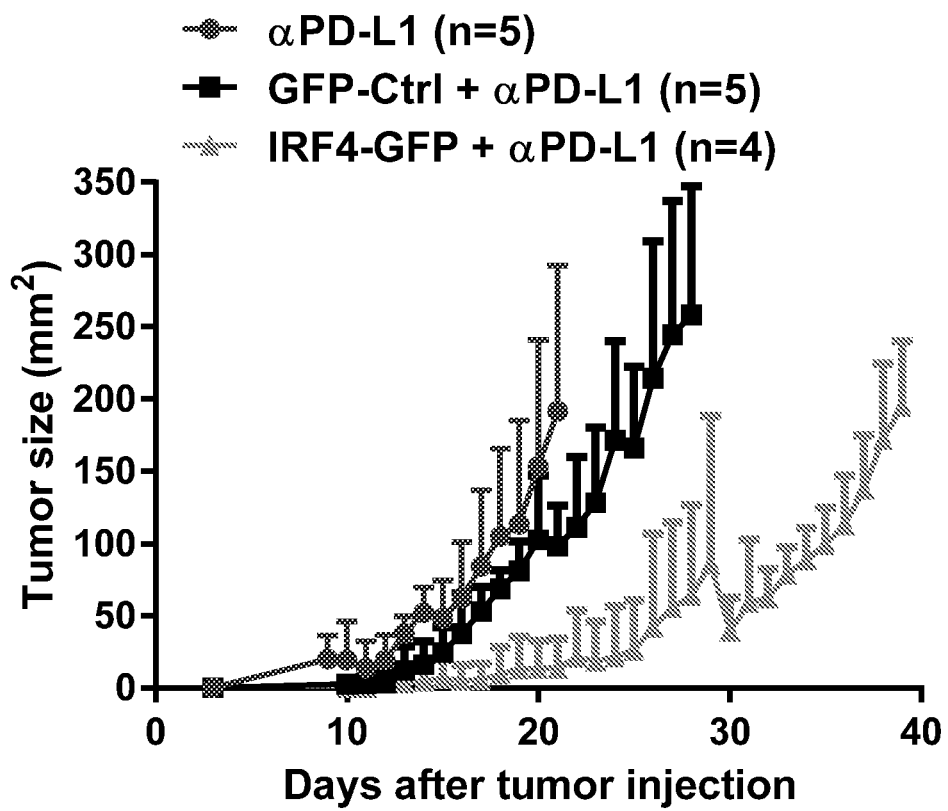
FIG. 3 is a graph depicting tumor suppression after in vivo administration of IRF4-engineered T cells combined with anti-PD-L1 mAb.

Example 3. IRF4-Engineered T Cells and Checkpoint Inhibitor Combination Therapy 10-week-old C57BL/6J male mice were s.c. injected with 5×10$^5$ B16-F10 melanoma cells on day 0, and were i.p. injected with 400 μg anti-PD-L1 mAb (clone 10F.9G2; Bio X Cell) on days 3, 6, and 9. On day 3, mice were also i.v. injected with cultured pmel-1 splenocytes containing 1×10$^6$ GFP-control (GFP-Ctrl+αPD-L1 group; n=5) or IRF4-GFP (IRF4-GFP+αPD-L1 group; n=4) transduced pmel-1 CD8+ T cells, or were not injected with cells (αPD-L1 group; n=5). Tumor growth (mean±SD) was measured over time for each group (FIG. 3). Results showed that adoptive transfer of melanoma-specific CD8+ T cells with increased IRF4 expression along with administration of a checkpoint inhibitor reduced tumor growth rate in mice more effectively than the checkpoint inhibitor alone.

Example 4. Combination Therapy of IRF4-Engineered T Cells, Checkpoint Inhibitor, and Cytokine Therapy 10-week-old C57BL/6J male mice were s.c. injected with 5×10$^5$ B16-F10 melanoma cells on day 0. Stating from day 9 when the tumors were established, mice were i.p. injected with 400 μg anti-PD-L1 mAb (clone 10F.9G2, Bio X Cell; on days 9, 12, and 15) and i.p. injected with 5 μg human IL-2 (Peprotech; twice a day from day 9 to day 29 or when mice were euthanized). On day 9, mice were also i.v. injected with cultured pmel-1 splenocytes containing 1 to 2 million GFP-control (GFP-Ctrl+αPD-L1+IL-2 group) or IRF4-GFP (IRF4-GFP+αPD-L1+IL-2 group) transduced pmel-1 CD8+ T cells, or were left without cell transfer (αPD-L1+IL-2 group).

Figure 4A:
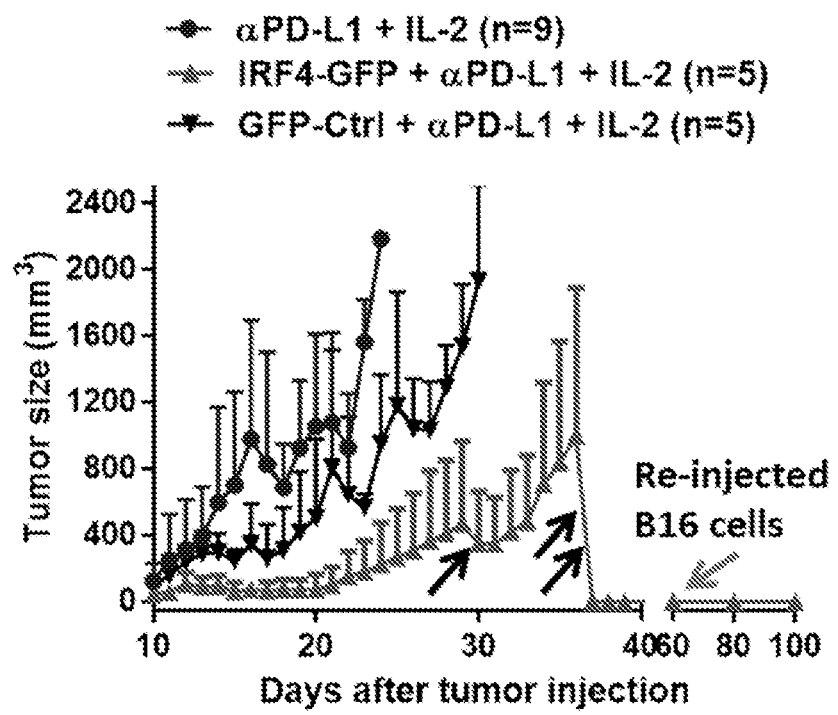
FIGS. 4A-4B are graphs depicting tumor suppression after in vivo administration of IRF4-engineered T cells combined with anti-PD-L1 mAb and IL-2. Mice treated with αPD-L1 mAb and IL-2, and further treated with pmel-1 CD8+ T cells expressing GFP alone (control) or IRF4 (experimental) were analyzed for growth of established tumors (FIG. 4A). Tumor infiltrating cells were analyzed by flow cytometry for percentage of IFN-γ producing cells (FIG. 4B).

FIG. 4A is a graph showing the tumor growth (mean±SD). The black arrows indicate the time point when 3 of 5 mice from the IRF4-GFP+αPD-L1+IL-2 group were euthanized (mice 1 of 5 through 3 of 5). On day 60, one tumor-free mouse (mouse 4 of 5) from the IRF4-GFP+αPD-L1+IL-2 group were s.c. injected again with 5×10$^5$ B16-F10 melanoma cells. Another mouse from the IRF4-GFP+αPD-L1+IL-2 group with tumor size 310 mm$^3$ on day 33 remains to date under tumor growth monitoring (mouse 5 of 5). Results showed that adoptive transfer of melanoma-specific CD8+ T cells with increased IRF4 expression combined with administration of a checkpoint inhibitor and IL-2 cytokine therapy suppress tumors in vivo more effectively than anti-PD-L1 mAb+IL-2 combination therapy alone. This was so even after mice were rechallenged with melanoma cells.

Figure 4B:
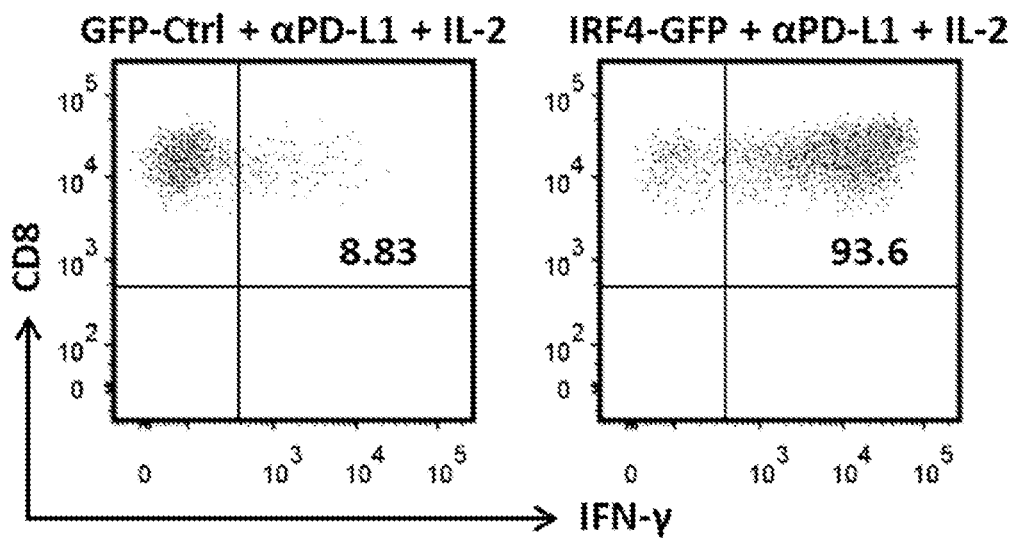

FIG. 4B shows data on mice from the pmel-1 CD8+ T cell injected groups (as indicated) which were euthanized on day 31. Tumor infiltrating cells were stimulated with PMA/Ionomycin plus Golgi-stop for 5 hours, followed by flow cytometric analysis. Representative plots show percent IFN-γ producing cells among GFP-Ctrl (left panel) or IRF4-GFP (right panel) transduced pmel-1 CD8+ T cells in tumors, gated on CD45$^+$Thy1.1$^+$CD8$^+$GFP$^+$ live cells. These results show that IRF4-overexpressing CD8+ T-cells produce increased levels of IFNγ compared to CD8+ T-cells which do not overexpress IRF4. Production of IFNγ indicated the T-cells were activated.

Example 5. IRF4 in T Cells Inhibits Syngeneic Melanoma Progression

Figure 5A:
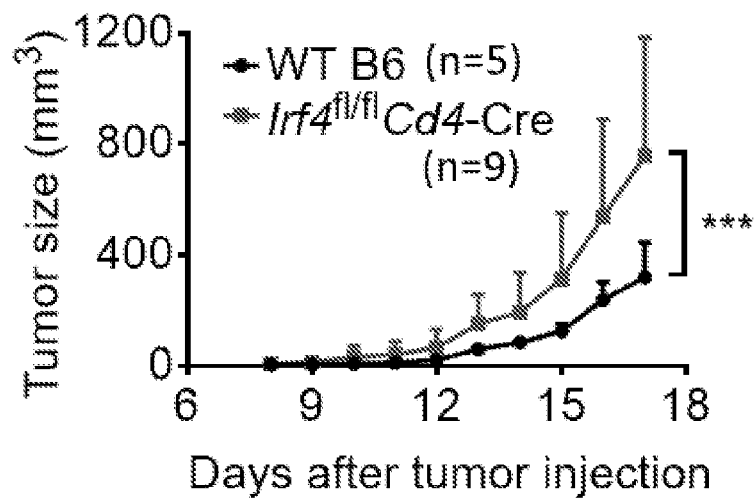
FIGS. 5A-5B show IRF4 deletion in T cells accelerates syngeneic melanoma progression. WT B6 (n=5) and Irf4$^{fl/fl}$Cd4-Cre (n=9) mice were s.c. injected with 2×10$^5$ B16-F10 melanoma cells.
Figure 5B:
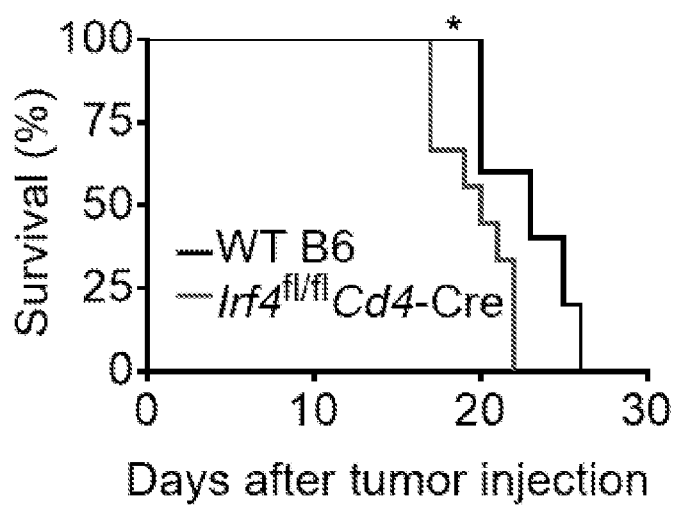

To determine the role of IRF4 in governing anti-tumor T cell function, B6 mice with T cell-specific IRF4 deletion (Irf4$^{fl/fl}$Cd4-Cre) and wild type (WT) B6 mice were s.c. injected with 2×10$^5$ B16-F10 syngeneic melanoma cells. When injected into B6 background mice, B16-F10 cells can gradually grow into tumors. As shown in FIG. 5A, B16-F10 tumor growth was significantly faster in Irf4$^{fl/fl}$Cd4-Cre B6 mice than that in WT B6 mice. Mice were euthanized when tumors reached to 2-cm-diameter. As shown in FIG. 5B, tumor-bearing Irf4"Cd4-Cre B6 mice had significantly shorter survival than tumor-bearing WT B6 mice. These findings indicate that T cell response against syngeneic B16-F10 tumors is significantly lost in Irf4$^{fl/fl}$Cd4-Cre mice.

Figure 6A:
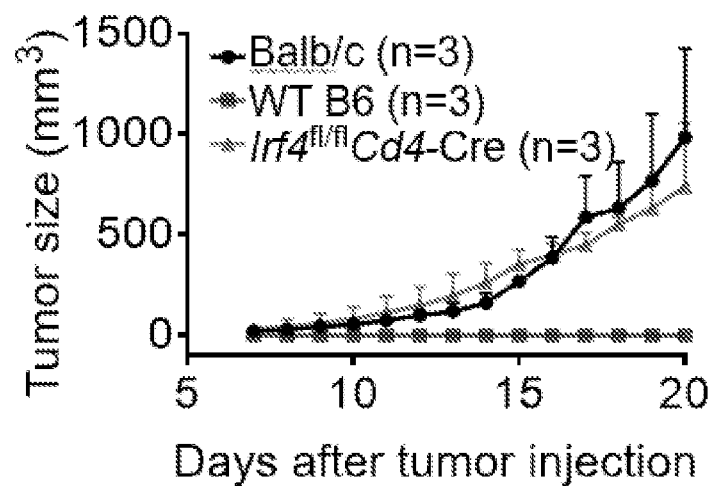
FIGS. 6A-6B show IRF4 deletion in T cells permits the growth of allogeneic CT26.WT colon cancer. Balb/c (n=3), WT B6 (n=3), and Irf4$^{fl/fl}$Cd4-Cre (n=3) mice were s.c. injected with 1×10$^6$ CT26.WT colon cancer cells (Balb/c background).
Figure 6B:
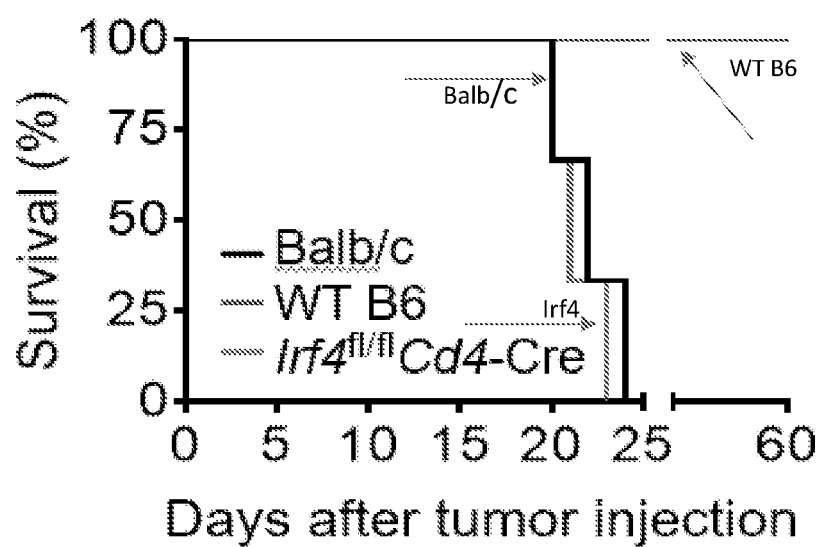
Figure 7:
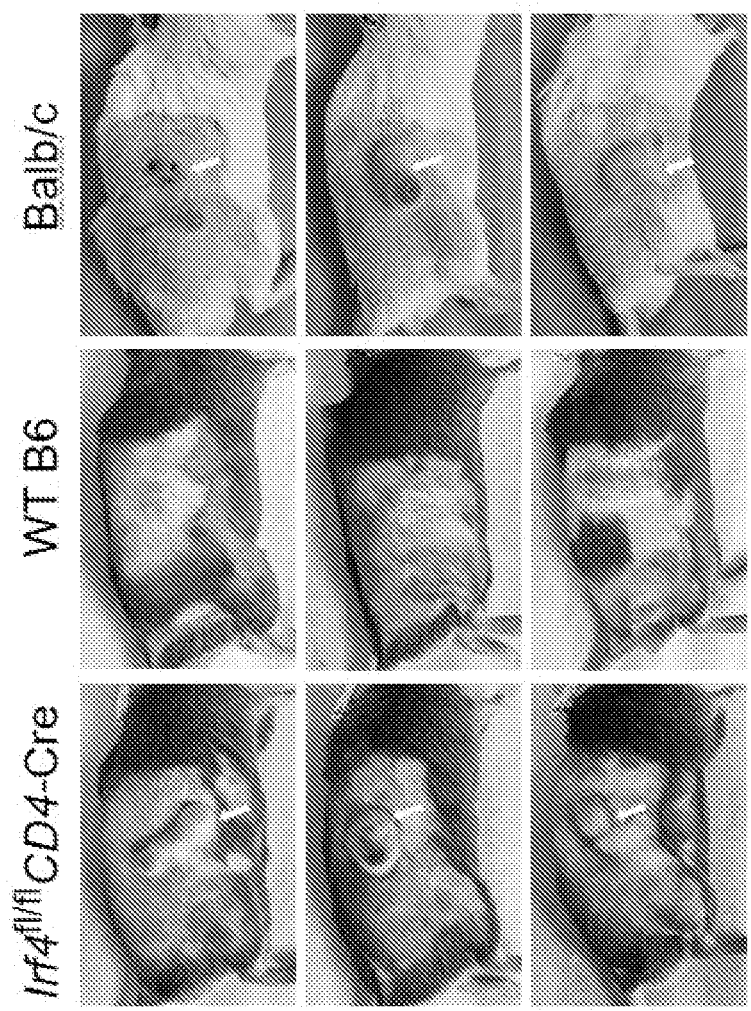
FIG. 7 shows IRF4 deletion in T cells permits the growth of allogeneic CT26.WT colon cancer, related to FIG. 2. Balb/c (n=3), WT B6 (n=3), and Irf4$^{fl/fl}$Cd4-Cre (n=3) mice were s.c. injected with 1×10$^6$ CT26.WT colon cancer cells (Balb/c background). Images show the tumor progression on mice at day 14 after tumor cell injection.

Example 6. IRF4 in T Cells is Require for Preventing the Growth of Allogeneic CT26.WT Colon Cancer Balb/c, WT B6, and Irf4$^{fl/fl}$Cd4-Cre B6 mice were s.c. injected with 1×10$^6$ CT26.WT colon cancer cells (Balb/c background). When injected into syngeneic Balb/c mice, CT26.WT cells gradually grow into tumors. When injected into allogeneic WT B6 mice, CT26.WT cells provoke a robust T cell response and never develop into tumors. When injected into allogeneic Irf4"'Cd4-Cre B6 mice, the tumor growth as well as the animal survival were similar to those in syngeneic Balb/c mice (FIGS. 6A, 6B and 7). These findings indicate that IRF4 in T cells is require for preventing the growth of allogeneic CT26.WT colon cancer.

Figure 8A:
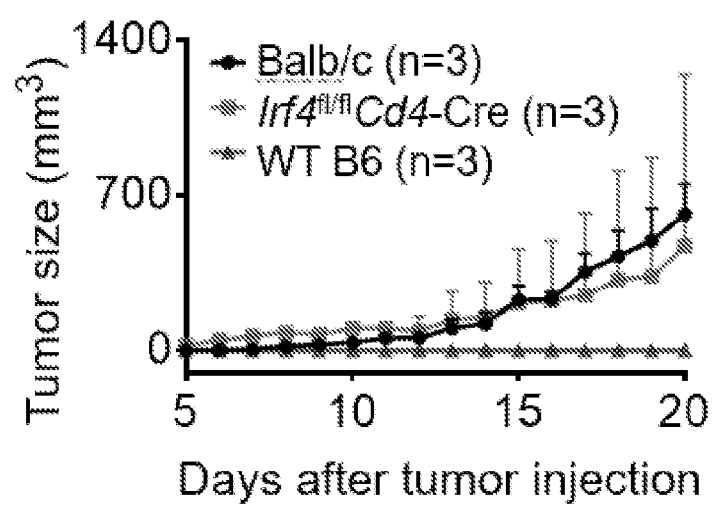
FIGS. 8A-8B show IRF4 deletion in T cells permits the growth of allogeneic A20 lymphoma. Balb/c (n=3), WT B6 (n=3), and Irf4$^{fl/fl}$Cd4-Cre (n=3) mice were s.c. injected with κ×10$^5$ A20 lymphoma cells (Balb/c background).
Figure 8B:
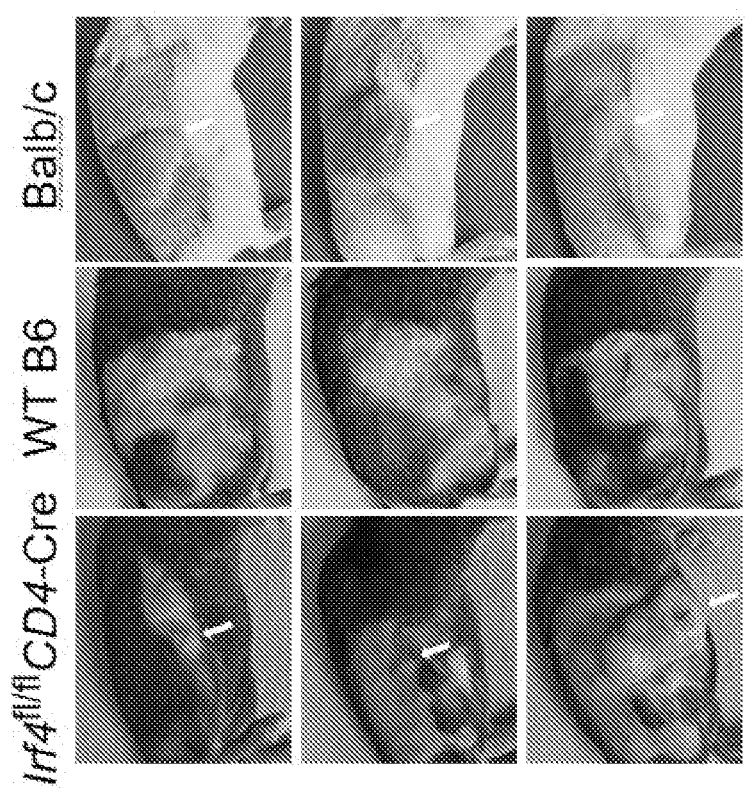

Example 7. IRF4 in T Cells is Require for Preventing the Growth of Allogeneic A20 Lymphoma Balb/c, WT B6, and Irf4$^{fl/fl}$Cd4-Cre B6 mice were s.c. injected with 5×10$^5$ A20 lymphoma cells (Balb/c background). When injected into syngeneic Balb/c mice, A20 cells gradually grow into tumors. When injected into allogeneic WT B6 mice, A20 cells provoke a robust T cell response and never develop into tumors. When injected into allogeneic Irf4$^{fl/fl}$Cd4-Cre B6 mice, the tumor growth as well as the animal survival were similar to those in syngeneic Balb/c mice (FIGS. 8A and 8B). These findings indicate that IRF4 in T cells is require for preventing the growth of allogeneic A20 lymphoma. Taken together, IRF4 in T cells is a master regulator for anti-tumor immunity.

SEQUENCES

SEQ ID NO: 1. Human IRF4 amino acid sequence (isoform 1).
```
MNLEGGGRGGEFGMSAVSCGNGKLRQWLIDQIDSGKYPGLVWENEEKSIFRIPWKHAGKQDYNREEDAALFKAWALFKGKFREGIDK
PDPPTWKTRLRCALNKSNDFEELVERSQLDISDPYKVYRIVPEGAKKGAKQLTLEDPQMSMSHPYTMTTPYPSLPAQQVHNYMMPPL
DRSWRDYVPDQPHPEIPYQCPMTFGPRGHHWQGPACENGCQVTGTFYACAPPESQAPGVPTEPSIRSAEALAFSDCRLHICLYYREI
LVKELTTSSPEGCRISHGHTYDASNLDQVLFPYPEDNGQRKNIEKLLSHLERGVVLWMAPDGLYAKRLCQSRIYWDGPLALCNDRPN
KLERDQTCKLFDTQQFLSELQAFAHHGRSLPRFQVTLCFGEEFPDPQRQRKLITAHVEPLLARQLYYFAQQNSGHFLRGYDLPEHIS
NPEDYHRSIRHSSIQE
```

SEQ ID NO: 2. Human IRF4 nucleic acid sequence (isoform 1).
```
ATGAACCTGGAGGGCGGCGGCCGAGGCGGAGAGTTCGGCATGAGCGCGGTGAGCTGCGGCAACGGGAAGCTCCGCCAGTGGCTGATC
GACCAGATCGACAGCGGCAAGTACCCCGGGCTGGTGTGGGAGAACGAGGAGAAGAGCATCTTCCGCATCCCCTGGAAGCACGCGGGC
AAGCAGGACTACAACCGCGAGGAGGACGCCGCGCTCTTCAAGGCTTGGGCACTGTTTAAAGGAAAGTTCCGAGAAGGCATCGACAAG
CCGGACCCTCCCACCTGGAAGACGCGCCTGCGGTGCGCTTTGAACAAGAGCAATGACTTTGAGGAACTGGTTGAGCGGAGCCAGCTG
GACATCTCAGACCCGTACAAAGTGTACAGGATTGTTCCTGAGGGAGCCAAAAAAGGAGCCAAGCAGCTCACCCTGGAGGACCCGCAG
ATGTCCATGAGCCACCCCTACACCATGACAACGCCTTACCCTTCGCTCCCAGCCCAGCAGGTTCACAACTACATGATGCCACCCCTC
GACCGAAGCTGGAGGGACTACGTCCCGGATCAGCCACACCCGGAAATCCCGTACCAATGTCCCATGACGTTTGGACCCCGCGGCCAC
CACTGGCAAGGCCCAGCTTGTGAAAATGGTTGCCAGGTGACAGGAACCTTTTATGCTTGTGCCCCACCTGAGTCCCAGGCTCCCGGA
GTCCCCACAGAGCCAAGCATAAGGTCTGCCGAAGCCTTGGCGTTCTCAGACTGCCGGCTGCACATCTGCCTGTACTACGGGAAATC
CTCGTGAAGGAGCTGACCACGTCCAGCCCCGAGGGCTGCCGGATCTCCCATGGACATACGTATGACGCCAGCAACCTGGACCAGGTC
CTGTTCCCCTACCCAGAGGACAATGGCCAGAGGAAAAACATTGAGAAGCTGCTGAGCCACCTGGAGAGGGGCGTGGTCCTCTGGATG
GCCCCCGACGGGCTCTATGCGAAAAGACTGTGCCAGAGCAGGATCTACTGGGACGGGCCCCTGGCGCTGTGCAACGACCGGCCCAAC
AAACTGGAGAGAGACCAGACCTGCAAGCTCTTTGACACACAGCAGTTCTTGTCAGAGCTGCAAGCGTTTGCTCACCACGGCCGCTCC
CTGCCAAGATTCCAGGTGACTCTATGCTTTGGAGAGGAGTTTCCAGACCCTCAGAGGCAAAGAAAGCTCATCACAGCTCACGTAGAA
CCTCTGCTAGCCAGACAACTATATTATTTTGCTCAACAAAACAGTGGACATTTCCTGAGGGGCTACGATTTACCAGAACACATCAGC
AATCCAGAAGATTACCACAGATCTATCCGCCATTCCTCTATTCAAGAATGA
```

SEQ ID NO: 3. Human IRF4 nucleic acid sequence (isoform 1) with 5' and 3' UTR sequences.
```
ACCTCGCACTCTCAGTTTCACCGCTCGATCTTGGGACCCACCGCTGCCCTCAGCTCCGAGTCCAGGGCGAGTGCAGAGCAGAGCGGG
CGGAGGACCCCGGGCGCGGGCGCGGACGGCACGCGGGCATGAACCTGGAGGGCGGCGGCCGAGGCGGAGAGTTCGGCATGAGCGCGG
TGAGCTGCGGCAACGGGAAGCTCCGCCAGTGGCTGATCGACCAGATCGACAGCGGCAAGTACCCCGGGCTGGTGTGGGAGAACGAGG
AGAAGAGCATCTTCCGCATCCCCTGGAAGCACGCGGGCAAGCAGGACTACAACCGCGAGGAGGACGCCGCGCTCTTCAAGGCTTGGG
CACTGTTTAAAGGAAAGTTCCGAGAAGGCATCGACAAGCCGGACCCTCCCACCTGGAAGACGCGGTGCGCTTTGAACAAGA
GCAATGACTTTGAGGAACTGGTTGAGCGGAGCCAGCTGGACATCTCAGACCCGTACAAAGTGTACAGGATTGTTCCTGAGGGAGCCA
AAAAAGGAGCCAAGCAGCTCACCCTGGAGGACCCGCAGATGTCCATGAGCCACCCCTACACCATGACAACGCCTTACCCTTCGCTCC
CAGCCCAGCAGGTTCACAACTACATGATGCCACCCCTCGACCGAAGCTGGAGGGACTACGTCCCGGATCAGCCACACCCGGAAATCC
CGTACCAATGTCCCATGACGTTTGGACCCCGCGGCCACCACTGGCAAGGCCCAGCTTGTGAAAATGGTTGCCAGGTGACAGGAACCT
TTTATGCTTGTGCCCCACCTGAGTCCCAGGCTCCCGGAGTCCCCACAGAGCCAAGCATAAGGTCTGCCGAAGCCTTGGCGTTCTCAG
ACTGCCGGCTGCACATCTGCCTGTACTACGGGAAATCCTCGTGAAGGAGCTGACCACGTCCAGCCCCGAGGGCTGCCGGATCTCCC
ATGGACATACGTATGACGCCAGCAACCTGGACCAGGTCCTGTTCCCCTACCCAGAGGACAATGGCCAGAGGAAAAACATTGAGAAGC
TGCTGAGCCACCTGGAGAGGGGCGTGGTCCTCTGGATGGCCCCCGACGGGCTCTATGCGAAAAGACTGTGCCAGAGCAGGATCTACT
GGGACGGGCCCCTGGCGCTGTGCAACGACCGGCCCAACAAACTGGAGAGAGACCAGACCTGCAAGCTCTTTGACACACAGCAGTTCT
TGTCAGAGCTGCAAGCGTTTGCTCACCACGGCCGCTCCCTGCCAAGATTCCAGGTGACTCTATGCTTTGGAGAGGAGTTTCCAGACC
CTCAGAGGCAAAGAAAGCTCATCACAGCTCACGTAGAACCTCTGCTAGCCAGACAACTATATTATTTTGCTCAACAAAACAGTGGAC
ATTTCCTGAGGGGCTACGATTTACCAGAACACATCAGCAATCCAGAAGATTACCACAGATCTATCCGCCATTCCTCTATTCAAGAAT
GAAAAATGTCAAGATGAGTGGTTTTCTTTTTCCTTTTTTTTTTTTTTTTGATACGGGGATACGGGGTCTTGCTCTGTCTCCCAGG
```

-continued

| SEQUENCES |
|---|
| CTGGAGTGCAGTGACACAATCTCAGCTCACTGTGACCTCCGCCTCCTGGGTTCAAGAGACTCTCCTGCCTCAGCCTCCCTGGTAGCT |
| GGGATTACAGGTGTGAGCCACTGCACCCACCCAAGACAAGTGATTTTCATTGTAAATATTTGACTTTAGTGAAAGCGTCCAATTGAC |
| TGCCCTCTTACTGTTTTGAGGAACTCAGAAGTGGAGATTTCAGTTCAGCGGTTCAGGAGAATTTGCGGCGAGACAAGCATGGAAAATC |
| AGTGACATCTGATTGGCAGATGAGCTTATTTCAAAAGGAAGGGTGGCTTTGCATTTCTTGTGTTCTATAGACTGCCATCATTGATGA |
| TCACTGTGAAAATTGACCAAGTGATGTGTTTACATTTACTGAAATGTGCTCTTTAATTTGTTGTAGATTAGGTCTTGCTGGAAGACA |
| GAGAAAACTTGCCTTTCAGTATTGACACTGACTAGAGTGATGACTGCTTGTAGGTATGTCTGTGCCATTTCTCAGGGAAGTAAGATG |
| TAAATTGAAGAAGCCTCACACGTAAAAGAAATGTATTAATGTATGTAGGACGTGCAGTTCTTGTGGAAGACACTTGCTGAGTGAAGG |
| AAATGAATCTTTGACTGAAGCCGTGCCTGTAGCCTTGGGGAGGCCCATCCCCCACCTGCCAGCGGTTTCCTGGTGTGGGTCCCTCTG |
| CCCCACCCTCCTTCCCATTGGCTTTCTCTCCTTGGCCTTTCCTGGAAGCCAGTTAGTAAACTTCCTATTTTCTTGAGTCAAAAAACA |
| TGAGCGCTACTCTTGGATGGGACATTTTTGTCTGTCCTACAATCTAGTAATGTCTAAGTAATGGTTAAGTTTTCTTGTTTCTGCATC |
| TTTTTGACCCTCATTCTTTAGAGATGCTAAAATTCTTCGCATAAAGAAGAAGAAATTAAGGAACATAAATCTTAATACTTGAACTGT |
| TGCCCTTCTGTCCAAGTACTTAACTATCTGTTCCCTTCCTCTGTGCCACGCTCCTCTGTTTGCTTGGCTGTCCAGCGATCAGCCATG |
| GCGACACTAAAGGAGGAGGAGCCGGGGACTCCCAGGCTGGAGAGCACTGCCAGGACCCACCACTGGAAGCAGGATGGAGCTGACTAC |
| GGAACTGCACACTCAGTGGGCTGTTTCTGCTTATTTCATCTGTTCTATGCTTCCTCGTGCCAATTATAGTTTGACAGGGCCTTAAAA |
| TTACTTGGCTTTTTCCAAATGCTTCTATTTATAGAATCCCAAAGACCTCCACTTGCTTAAGTATACCTATCACTTACATTTTTGTGG |
| TTTTGAGAAAGTACAGCAGTAGACTGGGGCGTCACCTCCAGGCCGTTTCTCATACTACAGGATATTTACTATTACTCCCAGGATCAG |
| CAGAAGATTGCGTAGCTCTCAAATGTGTGTTCCTGCTTTTCTAATGGATATTTTAAATTCATTCAACAAGCACCTAGTAAGTGCCTG |
| CTGTATCCCTACATTACACAGTTCAGCCTTTATCAAGCTTAGTGAGCAGTGAGCACTGAAACATTATTTTTTAATGTTTAAAAAGTT |
| TCTAATATTAAAGTCAGAATATTAATACAATTAATATTAATATTAACTACAGAAAAGACAAACAGTAGAGAACAGCAAAAAAATAAA |
| AAGGATCTCCTTTTTTCCCAGCCCAAATTCTCCTCTCTAAAAGTGTCCACAAGAAGGGGTGTTTATTCTTCCAACACATTTCACTTT |
| TCTGTAAATATACATAAACTTAAAAAGAAAACCTCATGGAGTCATCTTGCACACACTTTCATGCAGTGCTCTTTGTAGCTAACAGTG |
| AAGATTTACCTCGTTCTGCTCAGAGGCCTTGCTGTGGAGCTCCACTGCCATGTACCCAGTAGGGTTTGACATTTCATTAGCCATGCA |
| ACATGGATATGTATTGGGCAGCAGACTGTGTTTCGTGAACTGCAGTGATGTATACATCTTATAGATGCAAAGTATTTTGGGGTATAT |
| TATCCTAAGGGAAGATAAAGATGATATTAAGAACTGCTGTTTCACGGGGCCCTTACCTGTGACCCTCTTTGCTGAAGAATATTTAAC |
| CCCACACAGCACTTCAAAGAAGCTGTCTTGGAAGTCTGTCTCAGGAGCACCCTGTCTTCTTAATTCTCCAAGCGGATGCTCCATTTC |
| AATTGCTTTGTGACTTCTTCTTCTTTGTTTTTTTAAATATTATGCTGCTTTAACAGTGGAGCTGAATTTCTGGAAAATGCTTCTTG |
| GCTGGGGCCACTACCTCCTTTCCTATCTTTACATCTATGTGTATGTTGACTTTTTAAAATTCTGAGTGATCCAGGGTATGACCTAGG |
| GAATGAACTAGCTATGAAATACTCAGGGTTAGGAATCCTAGCACTTGTCTCCAGGACTCTGAAAAGGAACGGCTTCCTCATTCCTTGT |
| CTTGATAAAGTGGAATTGGCAAACTAGAATTTAGTTTGTACTCAGTGGACAGTGCTGTTGAAGATTTGAGGACTTGTTAAAGAGCAC |
| TGGGTCATATGGAAAAAATGTATGTGTCTCCCAGGTGCATTTCTTGGTTTATGTCTTGTTCTTGAGATTTTGTATATTTAGGAAAAC |
| CTCAAGCAGTAATTAATATCTCCTGGAACACTATAGAGAACCAAGTGACCGACTCATTTACAACTGAAACCTAGGAAGCCCCTGAGT |
| CCTGAGCGAAAACAGGAGAGTTAGTCGCCCTACAGGAAACCCGACTAGACTATTGGGTATGAACTAAAAAGAGACTGTGCCATGGTG |
| AGAAAAATGTAAAATCCTACAGTGGAATGAGCAGCCCTTACAGTGTTGTTACCACCAAGGGCAGGTAGGTATTAGTGTTTGAAAAAG |
| CTGGTCTTTGAGCGAGGGCATAAATACAGCTAGCCCCAGGGGTGGAACAACTGTGGGAGTCTTGGGTACTCGCACCTCTTGGCTTTG |
| TTGATGCTCCGCCAGGAAGGCCACTTGTGTGCGTGTCAGTTACTTTTTTAGTAACAATTCAGATCCAGTGTAAACTTCCGTTCAT |
| TGCTCTCCAGTCACATGCCCCCACTTCCCCACAGGTGAAAGTTTTTCTGAAAGTGTTGGGATTGGTTAAGGTCTTTATTTGTATTAC |
| GTATCTCCCCAAGTCCTCTGTGGCCAGCTGCATCTGTCTGAATGGTGCGTGAAGGCTCTCAGACCTTACACACCATTTTGTAAGTTA |
| TGTTTTACATGCCCCGTTTTTGAGACTGATCTCGATGCAGGTGGATCTCCTTGAGATCCTGATAGCCTGTTACAGGAATGAAGTAAA |
| GGTCAGTTTTTTTTGTATTGATTTTCACAGCTTTGAGGAACATGCATAAGAAATGTAGCTGAAGTAGAGGGGACGTGAGAGAAGGGC |
| CAGGCCGGCAGGCCAACCCTCCTCAATGGAAATTCCCGTGTTGCTTCAAACTGAGACAGATGGGACTTAACAGGCAATGGGTCCA |
| CTTCCCCCTCTTCAGCATCCCCCGTACCCCACTTTTTGCTGAAAGAACTGCCAGCAGGTAGGACCCCAGAGGCCCCCAAATGAAAGC |
| TTGAATTTCCCCTACTGGCTCTGCGTTTTGCTGAGATCTGTAGGAAAGGATGCTTCACAAACTGAGGTAGATAATGCTATGCTGTCG |
| TTGGTATACATCATGAATTTTTATGTAAATTGCTCTGCAAAGCAAATTGATATGTTTGATAAATTTATGTTTTAGGTAAATAAAAA |
| CTTTTAAAAAGTTGTT |

SEQ ID NO: 4. Human IRF4 amino acid sequence (isoform 2).
MNLEGGGRGGEFGMSAVSCGNGKLRQWLIDQIDSGKYPGLVWENEEKSIFRIPWKHAGKQDYNREEDAALFKAWALFKGKFREGIDK
PDPPTWKTRLRCALNKSNDFEELVERSQLDISDPYKVYRIVPEGAKKGAKQLTLEDPQMSMSHPYTMTTPYPSLPAQVHNYMMPPLD
RSWRDYVPDQPHPEIPYQCPMTFGPRGHHWQGPACENGCQVTGTFYACAPPESQAPGVPTEPSIRSAEALAFSDCRLHICLYYREIL
VKELTTSSPEGCRISHGHTYDASNLDQVLFPYPEDNGQRKNIEKLLSHLERGVVLWMAPDGLYAKRLCQSRIYWDGPLALCNDRPNK
LERDQTCKLFDTQQFLSELQAFAHHGRSLPRFQVTLCFGEEFPDPQRQRKLITAHVEPLLARQLYYFAQQNSGHFLRGYDLPEHISN
PEDYHRSIRHSSIQE SEQ ID NO: 5. Human IRF4 nucleic acid sequence (isoform 2).
ATGAACCTGGAGGGCGGCGGCCGAGGCGGAGAGTTCGGCATGAGCGCGGTGAGCTGCGGCAACGGGAAGCTCCGCCAGTGGCTGATC
GACCAGATCGACAGCGGCAAGTACCCCGGGCTGGTGTGGGAGAACGAGGAGAAGAGCATCTTCCGCATCCCCTGGAAGCACGCGGGC
AAGCAGGACTACAACCGCGAGGAGGACGCCGCGCTCTTCAAGGCTTGGGCACTGTTTAAAGGAAAGTTCCGAGAAGGCATCGACAAG
CCGGACCCTCCCACCTGGAAGACGCGCCTGCGGTGCGCTTTGAACAAGAGCAATGACTTTGAGGAACTGGTTGAGCGGAGCCAGCTG
GACATCTCAGACCCGTACAAAGTGTACAGGATTGTTCCTGAGGGAGCCAAAAAAGGAGCCAAGCAGCTCACCCTGGAGGACCCGCAG
ATGTCCATGAGCCACCCCTACACCATGACAACGCCTTACCCTTCGCTCCCAGCCCAGGTTCACAACTACATGATGCCACCCCTCGAC
CGAAGCTGGAGGGACTACGTCCCGGATCAGCCACACCCGGAAATCCCGTACCAATGTCCCATGACGTTTGGACCCCGCGGCCACCAC
TGGCAAGGCCCAGCTTGTGAAAATGGTTGCCAGGTGACAGGAACCTTTTATGCTTGCGCCCCACCTGAGTCCCAGGCTCCCGGAGTC
CCCACAGAGCCAAGCATAAGGTCTGCCGAAGCCTTGGCGTTCTCAGACTGCCGGCTGCACATCTGCCTGTACTACCGGGAAATCCTC
GTGAAGGAGCTGACCACGTCCAGCCCCGAGGGCTGCCGGATCTCCCATGGACATACGTATGACGCCAGCAACCTGGACCAGGTCCTG
TTCCCCTACCCAGAGGACAATGGCCAGAGGAAAAACATTGAGAAGCTGCTGAGCCACCTGGAGAGGGGCGTGGTCCTCTGGATGGCC
CCCGACGGGCTCTATGCGAAAAGACTGTGCCAGAGCAGGATCTACTGGGACGGGCCCCTGGCGCTGTGCAACGACCGGCCCAACAAA
CTGGAGAGAGACCAGACCTGCAAGCTCTTTGACACACAGCAGTTCTTGTCAGAGCTGCAAGCGTTTGCTCACCACGGCCGCTCCCTG
CCAAGATTCCAGGTGACTCTATGCTTTGGAGAGGAGTTTCCAGACCCTCAGAGGCAAAGAAAGCTCATCACAGCTCACGTAGAACCT
CTGCTAGCCAGACAACTATATTATTTTGCTCAACAAAACAGTGGACATTTCCTGAGGGGCTACGATTTACCAGAACACATCAGCAAT
CCAGAAGATTACCACAGATCTATCCGCCATTCCTCTATTCAAGAATGA SEQ ID NO: 6. Human IRF4 nucleic acid sequence (isoform 2) with 5' and 3' UTR
sequences.
ACCTCGCACTCTCAGTTTCACCGCTCGATCTTGGGACCCACCGCTGCCCTCAGCTCCGAGTCCAGGGCGAGTGCAGAGCAGAGCGGG
CGGAGGACCCCGGGCGCGGGCGCGGACGGCACGCGGGCATGAACCTGGAGGGCGGCGGCCGAGGCGGAGAGTTCGGCATGAGCGCGG
TGAGCTGCGGCAACGGGAAGCTCCGCCAGTGGCTGATCGACCAGATCGACAGCGGCAAGTACCCCGGGCTGGTGTGGGAGAACGAGG
AGAAGAGCATCTTCCGCATCCCCTGGAAGCACGCGGGCAAGCAGGACTACAACCGCGAGGAGGACGCCGCGCTCTTCAAGGCTTGGG

SEQUENCES

```
CACTGTTTAAAGGAAAGTTCCGAGAAGGCATCGACAAGCCGGACCCTCCCACCTGGAAGACGCGCCTGCGGTGCGCTTTGAACAAGA
GCAATGACTTTGAGGAACTGGTTGAGCGGAGCCAGCTGGACATCTCAGACCCGTACAAAGTGTACAGGATTGTTCCTGAGGGAGCCA
AAAAAGGAGCCAAGCAGCTCACCCTGGAGGACCCGCAGATGTCCATGAGCCACCCCTACACCATGACAACGCCTTACCCTTCGCTCC
CAGCCCAGGTTCACAACTACATGATGCCACCCCTCGACCGAAGCTGGAGGGACTACGTCCCGGATCAGCCACACCCGGAAATCCCGT
ACCAATGTCCCATGACGTTTGGACCCCGCGGCCACCACTGGCAAGGCCCAGCTTGTGAAAATGGTTGCCAGGTGACAGGAACCTTTT
ATGCTTGTGCCCCACCTGAGTCCCAGGCTCCCGGAGTCCCCACAGAGCCAAGCATAAGGTCTGCCGAAGCCTTGGCGTTCTCAGACT
GCCGGCTGCACATCTGCCTGTACTACCGGGAAATCCTCGTGAAGGAGCTGACCACGTCCAGCCCCGAGGGCTGCCGGATCTCCCATG
GACATACGTATGACGCCAGCAACCTGGACCAGGTCCTGTTCCCCTACCCAGAGGACAATGGCCAGAGGAAAAACATTGAGAAGCTGC
TGAGCCACCTGGAGAGGGCGTGGTCCTCTGGATGGCCCCGACGGGCTCTATGCGAAAAGACTGTGCCAGAGCAGGATCTACTGGG
ACGGGCCCCTGGCGCTGTGCAACGACCGGCCCAACAAACTGGAGAGAGACCAGACCTGCAAGCTCTTTGACACACAGCAGTTCTTGT
CAGAGCTGCAAGCGTTTGCTCACCACGGCCGCTCCCTGCCAAGATTCCAGGTGACTCTATGCTTTGGAGAGGAGTTTCCAGACCCTC
AGAGGCAAAGAAAGCTCATCACAGCTCACGTAGAACCTCTGCTAGCCAGACAACTATATTATTTTGCTCAACAAACAGTGGACATT
TCCTGAGGGGCTACGATTTACCAGAACACATCAGCAATCAGAAGATTACCACAGATCTATCCGCCATTCCTCTATTCAAGAATGAA
AAATGTCAAGATGAGTGGTTTTCTTTTTCCTTTTTTTTTTTTTTTGATACGGGGATACGGGGTCTTGCTCTGTCTCCCAGGCTG
GAGTGCAGTGACACAATCTCAGCTCACTGTGACCTCCGCCTCCTGGGTTCAAGAGACTCTCCTGCCTCAGCCTCCCTGGTAGCTGGG
ATTACAGGTGTGAGCCACTGCACCCACCCAAGACAAGTGATTTTCATTGTAAATATTTGACTTTAGTGAAAGCGTCCAATTGACTGC
CCTCTTACTGTTTGAGGAACTCAGAAGTGGAGATTTCAGTTCAGCGGTTGAGGAGAATTGCGGCGAGACAAGCATGGAAAATCAGT
GACATCTGATTGGCAGATGAGCTTATTTCAAAAGGAAGGGTGGCTTTGCATTTCTTGTGTTCTATAGACTGCCATCATTGATGATCA
CTGTGAAAATTGACCAAGTGATGTGTTTACATTTACTGAAATGTGCTCTTTAATTTGTTGTAGATTAGGTCTTGCTGGAAGACAGAG
AAAACTTGCCTTTCAGTATTGACACTGACTAGAGTGATGACTGCTTGTAGGTATGTCTGTGCCATTTCTCAGGGAAGTAAGATGTAA
ATTGAAGAAGCCTCACACGTAAAAGAAATGTATTAATGTATGTAGGAGCTGCAGTTCTTGTGGAAGACACTTGCTGAGTGAAGGAAA
TGAATCTTTGACTGAAGCCGTGCCTGTAGCCTTGGGGAGGCCCATCCCCCACCTGCCAGCGGTTTCCTGGTGTGGGTCCCTCTGCCC
CACCCTCCTTCCCATTGGCTTTCTCTCCTTGGCCTTTCCTGGAAGCCAGTTAGTAAACTTCCTATTTTCTTGAGTCAAAAACATGA
GCGCTACTCTTGGATGGGACATTTTTGTCTGTCCTACAATCTAGTAATGTCTAAGTAATGGTTAAGTTTTCTTGTTTCTGCATCTTT
TTGACCCTCATTCTTTAGAGATGCTAAAATTCTTCGCATAAAGAAGAAGAAATTAAGGAACATAAATCTTAATACTTGAACTGTTGC
CCTTCTGTCCAAGTACTTAACTATCTGTTCCCTTCCTCTGTGCCACGCTCCTCTGTTTGCTTGGCTGTCCAGCGATCAGCCATGGCG
ACACTAAAGGAGGAGGAGCCGGGGACTCCCAGGCTGGAGAGCACTGCCAGGACCCACCACTGGAAGCAGGATGGAGCTGACTACGGA
ACTGCACACTCAGTGGGCTGTTTCTGCTTATTTCATCTGTTCTATGCTTCCTCGTGCCAATTATAGTTTGACAGGGCCTTAAAATTA
CTTGGCTTTTTCCAAATGCTTCTATTTATAGAATCCCAAAGACCTCCACTTGCTTAAGTATACCTATCACTTACATTTTTGTGGTTT
TGAGAAAGTACAGCAGTAGACTGGGGCGTCACCTCCAGGCCGTTTCTCATACTACAGGATATTTACTATTACTCCCAGGATCAGCAG
AAGATTGCGTAGCTCTCAAATGTGTGTTCCTGCTTTTCTAATGGATATTTTAAATTCATTCAACAAGCACCTAGTAAGTGCCTGCTG
TATCCCTACATTACACAGTTCAGCCTTTATCAAGCTTAGTGAGCAGTGACCACATTATTTTTTAATGTTTAAAAAGTTTCT
AATATTTAAAGTCAGAATATTAATACAATTAATATTAATATTAACTACAGAAAAGACAAACAGTAGAGAACAGCAAAAAAATAAAAAG
GATCTCCTTTTTTCCCAGCCCAAATTCTCCTCTCTAAAAGTGTCCACAAGAAGGGGTGTTATTCTTCCAACACATTTCACTTTTCT
GTAAATATACATAAACTTAAAAAGAAAACCTCATGGAGTCATCTTGCACACACTTTCATGCAGTGCTCTTTGTAGCTAACAGTGAAG
ATTTACCTCGTTCTGCTCAGAGGCCTTGCTGTGGAGCTCCACTGCCATGTACCCAGTAGGGTTTGACATTTCATTAGCCATGCAACA
TGGATATGTATTGGGCAGCAGACTGTGTTTCGTGAACTGCAGTGATGTATACATCTTATAGATGCAAAGTATTTTGGGGTATATTAT
CCTAAGGGAAGATAAAGATGATATTAAGAACTGCTGTTTCACGGGGCCCTTACCTGTGACCCTCTTTGCTGAAGAATATTTAACCCC
ACACAGCACTTCAAAGAAGCTGTCTTGGAAGTCTGTCTCAGGAGCACCCTGTCTTCTTAATTCTCCAAGCGGATGCTCCATTTCAAT
TGCTTTGTGACTTCTTCTTCTTTGTTTTTTTAAATATTATGCTGCTTTAACAGTGGAGCTGAATTTTCTGGAAAATGCTTCTTGGCT
GGGGCCACTACCTCCTTTCCTATCTTTACATCTATGTGTATGTTGACTTTTTAAAATTCTGAGTGATCCAGGGTATGACCTAGGGAA
TGAACTAGCTATGAAATACTCAGGGTTAGGAATCCTAGCACTTGTCTCAGGACTCTGAAAAGGAACGGCTTCCTCATTCCTTGTCTT
GATAAAGTGGAATTGGCAAACTAGAATTTAGTTTGTACTCAGTGGACAGTGCTGTTGAAGATTTGAGGACTTGTTAAAGAGCACTGG
GTCATATGGAAAAAATGTATGTGTCTCCCAGGTGCATTTCTTGGTTTATGTCTTGTTCTTGAGATTTTGTATATTTAGGAAAACCTC
AAGCAGTAATTAATATCTCCTGGAACACTATAGAGAACAAGATGACCGACTCATTTACAACTAGGAAGCCCCTGAGTCCT
GAGCGAAAACAGGAGAGTTAGTCGCCCTACAGGAAACCCAGCTAGACTATTGGGTATGAACTAAAAAGAGACTGTGCCATGGTGAGA
AAAATGTAAAATCCTACAGTGGAATGAGCAGCCCTTACAGTGTTGTTACCACCAAGGGCAGGTAGGTATTAGTGTTTGAAAAAGCTG
GTCTTTGAGCGAGGGCATAAATACAGCTAGCCCCAGGGGTGGAACAACTGTGGGAGTCTTGGGTACTCGCACCTCTTGGCTTTGTTG
ATGCTCCGCCAGGAAGGCCACTTGTGTGTGCGTGCAGTTACTTTTTAGTAACAATTCAGATCCAGTGTAAACTTCCGTTCATTGC
TCTCCAGTCACATGCCCCCACTTCCCCACAGGTGAAAGTTTTTCTGAAAGTGTTGGGATTGGTTAAGGTCTTTATTTGTATTACGTA
TCTCCCCAAGTCCTCTGTGGCCAGCTGCATCTGTCTGAATGGTGCGTGAAGGCTCTCAGACCTTACACACCATTTTGTAAGTTATGT
TTTACATGCCCCGTTTTTGAGACTGATCTCGATGCAGGTGGATCTCCTTGAGATCCTGATAGCCTGTTACAGGAATGAAGTAAAGGT
CAGTTTTTTTTGTATTGATTTTCACAGCTTTGAGGAACATGCATAAGAAATGTAGCTGAAGTAGAGGGGACGTGAGAGAAGGGCCAG
GCCGGCAGGCCAACCCTCCTCCAATGGAAATTCCCGTGTTGCTTCAAACTGAGACAGATGGGACTTAACAGGCAATGGGGTCCACTT
CCCCCTCTTCAGCATCCCCCGTACCCCACTTTTTGCTGAAAGAACTGCCAGCAGGTAGGACCCCAGAGGCCCCAAATGAAAGCTTG
AATTTCCCCTACTGGCTCTGCGTTTTGCTGAGATCTGTAGGAAAGGATGCTTCACAAACTGAGGTAGATAATGCTATGCTGTCGTTG
GTATACATCATGAATTTTTATGTAAATTGCTCTGCAAAGCAAATTGATATGTTTGATAAATTTATGTTTTTAGGTAAATAAAAACTT
TTAAAAAGTTGTT
```

Publications cited herein are hereby specifically incorporated by reference in their entireties and at least for the material for which they are cited.

It should be understood that while the present disclosure has been provided in detail with respect to certain illustrative and specific aspects thereof, it should not be considered limited to such, as numerous modifications are possible without departing from the broad spirit and scope of the present disclosure as defined in the appended claims. It is, therefore, intended that the appended claims cover all such equivalent variations as fall within the true spirit and scope of the invention.

What is claimed is:

1. A method to treat cancer in a subject comprising administering to the subject a therapeutically effective amount of T-cells of the subject having increased IRF4 polypeptide expression compared to unmodified T-cells from the subject; wherein the increased IRF4 polypeptide expression comprises introducing into the T-cells a polynucleotide comprising a nucleic acid sequence which is at least 70% identical to SEQ ID NO: 2.

2. The method of claim 1, wherein the IRF4 polypeptide comprises an amino acid sequence which is at least 80% identical to SEQ ID NO: 1.

3. The method of claim 1, wherein at least about one million T-cells are administered.

4. The method of claim 1, wherein the IRF4 polypeptide expression is increased by at least 50% compared to the unmodified T-cells from the subject.

5. The method of claim 1, wherein the T-cells comprise tumor-specific T-cells.

6. The method of claim 1, wherein the T-cells comprise CD8+T-cells.

7. The method of claim 1, wherein the administering comprises intratumoral injection.

8. The method of claim 1, wherein the polynucleotide is comprised in a viral vector.

9. The method of claim 1, further comprising administering one or more additional anti-cancer therapeutics.

10. The method of claim 9, wherein the one or more additional anti-cancer therapeutics comprises a T-cell modulator, a cell-cycle regulator, or combinations thereof.

11. The method of claim 10, wherein the T-cell modulator comprises IL-2.

12. The method of claim 10, wherein the cell-cycle regulator comprises an anti-PD-L1 antibody, an anti-PD-1 antibody, an anti-CTLA-4 antibody, or combinations thereof.

13. The method of claim 9, wherein the one or more additional anti-cancer therapeutics comprises IL-2 and an anti-PD-L1 antibody.

14. The method of claim 1, wherein the cancer comprises melanoma, breast cancer, colon cancer, or lymphoma.

* * * * *

SEQUENCE LISTING

<160> NUMBER OF SEQ ID NOS: 6

<210> SEQ ID NO 1
<211> LENGTH: 451

```
<212> TYPE: PRT
<213> ORGANISM: Artificial Sequence
<220> FEATURE:
<223> OTHER INFORMATION: Synthetic construct

<400> SEQUENCE: 1

Met Asn Leu Glu Gly Gly Gly Arg Gly Gly Glu Phe Gly Met Ser Ala
1               5                   10                  15

Val Ser Cys Gly Asn Gly Lys Leu Arg Gln Trp Leu Ile Asp Gln Ile
            20                  25                  30

Asp Ser Gly Lys Tyr Pro Gly Leu Val Trp Glu Asn Glu Glu Lys Ser
        35                  40                  45

Ile Phe Arg Ile Pro Trp Lys His Ala Gly Lys Gln Asp Tyr Asn Arg
    50                  55                  60

Glu Glu Asp Ala Ala Leu Phe Lys Ala Trp Ala Leu Phe Lys Gly Lys
65                  70                  75                  80

Phe Arg Glu Gly Ile Asp Lys Pro Asp Pro Thr Trp Lys Thr Arg
                85                  90                  95

Leu Arg Cys Ala Leu Asn Lys Ser Asn Asp Phe Glu Glu Leu Val Glu
                100                 105                 110

Arg Ser Gln Leu Asp Ile Ser Asp Pro Tyr Lys Val Tyr Arg Ile Val
            115                 120                 125

Pro Glu Gly Ala Lys Lys Gly Ala Lys Gln Leu Thr Leu Glu Asp Pro
        130                 135                 140

Gln Met Ser Met Ser His Pro Tyr Thr Met Thr Thr Pro Tyr Pro Ser
145                 150                 155                 160

Leu Pro Ala Gln Gln Val His Asn Tyr Met Met Pro Pro Leu Asp Arg
                165                 170                 175

Ser Trp Arg Asp Tyr Val Pro Asp Gln Pro His Pro Glu Ile Pro Tyr
            180                 185                 190

Gln Cys Pro Met Thr Phe Gly Pro Arg Gly His His Trp Gln Gly Pro
        195                 200                 205

Ala Cys Glu Asn Gly Cys Gln Val Thr Gly Thr Phe Tyr Ala Cys Ala
    210                 215                 220

Pro Pro Glu Ser Gln Ala Pro Gly Val Pro Thr Glu Pro Ser Ile Arg
225                 230                 235                 240

Ser Ala Glu Ala Leu Ala Phe Ser Asp Cys Arg Leu His Ile Cys Leu
                245                 250                 255

Tyr Tyr Arg Glu Ile Leu Val Lys Glu Leu Thr Thr Ser Ser Pro Glu
            260                 265                 270

Gly Cys Arg Ile Ser His Gly His Thr Tyr Asp Ala Ser Asn Leu Asp
        275                 280                 285

Gln Val Leu Phe Pro Tyr Pro Glu Asp Asn Gly Gln Arg Lys Asn Ile
    290                 295                 300

Glu Lys Leu Leu Ser His Leu Glu Arg Gly Val Val Leu Trp Met Ala
305                 310                 315                 320

Pro Asp Gly Leu Tyr Ala Lys Arg Leu Cys Gln Ser Arg Ile Tyr Trp
                325                 330                 335

Asp Gly Pro Leu Ala Leu Cys Asn Asp Arg Pro Asn Lys Leu Glu Arg
            340                 345                 350

Asp Gln Thr Cys Lys Leu Phe Asp Thr Gln Gln Phe Leu Ser Glu Leu
        355                 360                 365

Gln Ala Phe Ala His His Gly Arg Ser Leu Pro Arg Phe Gln Val Thr
    370                 375                 380
```

```
Leu Cys Phe Gly Glu Glu Phe Pro Asp Pro Gln Arg Gln Arg Lys Leu
385                 390                 395                 400

Ile Thr Ala His Val Glu Pro Leu Leu Ala Arg Gln Leu Tyr Tyr Phe
                405                 410                 415

Ala Gln Gln Asn Ser Gly His Phe Leu Arg Gly Tyr Asp Leu Pro Glu
            420                 425                 430

His Ile Ser Asn Pro Glu Asp Tyr His Arg Ser Ile Arg His Ser Ser
        435                 440                 445

Ile Gln Glu
    450

<210> SEQ ID NO 2
<211> LENGTH: 1356
<212> TYPE: DNA
<213> ORGANISM: Artificial Sequence
<220> FEATURE:
<223> OTHER INFORMATION: Synthetic construct

<400> SEQUENCE: 2
atgaacctgg agggcggcgg ccgaggcgga gagttcggca tgagcgcggt gagctgcggc        60
aacgggaagc tccgccagtg gctgatcgac cagatcgaca gcggcaagta ccccgggctg       120
gtgtgggaga acgaggagaa gagcatcttc cgcatcccct ggaagcacgc gggcaagcag       180
gactacaacc gcgaggagga cgccgcgctc ttcaaggctt gggcactgtt taaaggaaag       240
ttccgagaag gcatcgacaa gccggaccct cccacctgga gacgcgcct gcggtgcgct       300 ttgaacaaga gcaatgactt tgaggaactg gttgagcgga gccagctgga catctcagac       360
ccgtacaaag tgtacaggat tgttcctgag ggagccaaaa aaggagccaa gcagctcacc       420
ctggaggacc gcagatgtc catgagccac ccctacacca tgacaacgcc ttacccttcg       480
ctcccagccc agcaggttca aactacatg atgccacccc tcgaccgaag ctggagggac       540
tacgtcccgg atcagccaca cccggaaatc ccgtaccaat gtccatgac gtttggaccc       600 cgcggccacc actggcaagg cccagcttgt gaaaatggtt gccaggtgac aggaaccttt       660
tatgcttgtg ccccacctga gtcccaggct cccggagtcc ccacagagcc aagcataagg       720
tctgccgaag ccttggcgtt ctcagactgc cggctgcaca tctgcctgta ctaccgggaa       780
atcctcgtga aggagctgac cacgtccagc cccgagggct gccggatctc ccatggacat       840
acgtatgacg ccagcaacct ggaccaggtc ctgttcccct acccaggga caatggccag       900 aggaaaaaca ttgagaagct gctgagccac ctggagaggg gcgtggtcct ctggatggcc       960
cccgacgggc tctatgcgaa aagactgtgc cagagcagga tctactggga cgggcccctg     1020
gcgctgtgca cgaccggcc caacaaactg gagagagacc agacctgcaa gctctttgac     1080
acacagcagt tcttgtcaga gctgcaagcg tttgctcacc acggccgctc cctgccaaga     1140
ttccaggtga ctctatgctt tggagaggag tttccagacc ctcagaggca agaaagctc     1200 atcacagctc acgtagaacc tctgctagcc agacaactat attatttgc tcaacaaaac     1260 agtggacatt tcctgagggg ctacgattta ccagaacaca tcagcaatcc agaagattac     1320
cacagatcta tccgccattc ctctattcaa gaatga                                1356

<210> SEQ ID NO 3
<211> LENGTH: 5323
<212> TYPE: DNA
<213> ORGANISM: Artificial Sequence
<220> FEATURE:
<223> OTHER INFORMATION: Synthetic construct
```

```
<400> SEQUENCE: 3
acctcgcact ctcagtttca ccgctcgatc ttgggaccca ccgctgccct cagctccgag      60
tccagggcga gtgcagagca gagcgggcgg aggaccccgg gcgcgggcgc ggacggcacg     120
cgggcatgaa cctggagggc ggcggccgag gcggagagtt cggcatgagc gcggtgagct     180
gcggcaacgg gaagctccgc cagtggctga tcgaccagat cgacagcggc aagtaccccg     240
ggctggtgtg ggagaacgag gagaagagca tcttccgcat cccctggaag cacgcgggca     300
agcaggacta caaccgcgag gaggacgccg cgctcttcaa ggcttgggca ctgtttaaag     360
gaaagttccg agaaggcatc gacaagccgg accctcccac ctggaagacg cgcctgcggt     420
gcgctttgaa caagagcaat gactttgagg aactggttga gcggagccag ctggacatct     480
cagacccgta caaagtgtac aggattgttc ctgagggagc caaaaaagga gccaagcagc     540
tcaccctgga ggacccgcag atgtccatga gccacccta ccatgacaa cgccttacc     600 cttcgctccc agcccagcag gttcacaact acatgatgcc accctcgac cgaagctgga     660 gggactacgt cccggatcag ccacacccgg aaatcccgta ccaatgtccc atgacgtttg     720
gaccccgcgg ccaccactgg caaggcccag cttgtgaaaa tggttgccag gtgacaggaa     780 cctttatgc ttgtgcccca cctgagtccc aggctcccgg agtccccaca gagccaagca     840
taaggtctgc cgaagccttg gcgttctcag actgccggct gcacatctgc ctgtactacc     900
gggaaatcct cgtgaaggag ctgaccacgt ccagccccga gggctgccgg atctcccatg     960
gacatacgta tgacgccagc aacctggacc aggtcctgtt ccctacccca gaggacaatg    1020
gccagaggaa aaacattgag aagctgctga gccacctgga gggggcgtg gtcctctgga    1080 tggcccccga cgggctctat gcgaaaagac tgtgccagag caggatctac tgggacgggc    1140
ccctggcgct gtgcaacgac cggcccaaca aactggagag agaccagacc tgcaagctct    1200
ttgacacaca gcagttcttg tcagagctgc aagcgtttgc tcaccacggc cgctccctgc    1260
caagattcca ggtgactcta tgctttggag aggagtttcc agaccctcag aggcaaagaa    1320
agctcatcac agctcacgta gaacctctgc tagccagaca actatattat tttgctcaac    1380
aaaacagtgg acatttcctg agggggctacg atttaccaga acacatcagc aatccagaag    1440
attaccacag atctatccgc cattcctcta ttcaagaatg aaaaatgtca agatgagtgg    1500
ttttcttttt ccttttttttt tttttttttt gatacgggga tacggggtct tgctctgtct    1560
cccaggctgg agtgcagtga cacaatctca gctcactgtg acctccgcct cctgggttca    1620
agagactctc ctgcctcagc ctccctggta gctgggatta caggtgtgag ccactgcacc    1680
cacccaagac aagtgatttt cattgtaaat atttgacttt agtgaaagcg tccaattgac    1740
tgccctctta ctgttttgag gaactcagaa gtggagattt cagttcagcg gttgaggaga    1800
attgcggcga gacaagcatg gaaaatcagt gacatctgat tggcagatga gcttatttca    1860
aaaggaaggg tggctttgca tttcttgtgt tctatagact gccatcattg atgatcactg    1920
tgaaaattga ccaagtgatg tgtttacatt tactgaaatg tgctctttaa tttgttgtag    1980
attaggtctt gctggaagac agagaaaact tgcctttcag tattgacact gactagagtg    2040
atgactgctt gtaggtatgt ctgtgccatt tctcagggaa gtaagatgta aattgaagaa    2100
gcctcacacg taaaagaaat gtattaatgt atgtaggagc tgcagttctt gtggaagaca    2160
cttgctgagt gaaggaaatg aatctttgac tgaagccgtg cctgtagcct tggggaggcc    2220 catccccac ctgccagcgg tttcctggtg tgggtccctc tgccccaccc tccttcccat    2280
tggctttctc tccttggcct ttcctggaag ccagttagta aacttcctat tttcttgagt    2340
```

```
caaaaaacat gagcgctact cttggatggg acattttttgt ctgtcctaca atctagtaat   2400
gtctaagtaa tggttaagtt ttcttgtttc tgcatctttt tgaccctcat tctttagaga   2460
tgctaaaatt cttcgcataa agaagaagaa attaaggaac ataaatctta atacttgaac   2520
tgttgccctt ctgtccaagt acttaactat ctgttccctt cctctgtgcc acgtcctct    2580 gtttgcttgg ctgtccagcg atcagccatg gcgacactaa aggaggagga gccggggact   2640
cccaggctgg agagcactgc caggacccac cactggaagc aggatggagc tgactacgga   2700
actgcacact cagtgggctg tttctgctta tttcatctgt tctatgcttc ctcgtgccaa   2760
ttatagtttg acagggcctt aaaattactt ggcttttcc aaatgcttct atttatagaa    2820
tcccaaagac ctccacttgc ttaagtatac ctatcactta catttttgtg gttttgagaa   2880
agtacagcag tagactgggg cgtcacctcc aggccgtttc tcatactaca ggatatttac   2940
tattactccc aggatcagca gaagattgcg tagctctcaa atgtgtgttc ctgcttttct   3000
aatggatatt ttaaattcat tcaacaagca cctagtaagt gcctgctgta tccctacatt   3060
acacagttca gcctttatca agcttagtga gcagtgagca ctgaaacatt attttttaat   3120
gtttaaaaag tttctaatat taaagtcaga atattaatac aattaatatt aatattaact   3180
acagaaaaga caaacagtag agaacagcaa aaaaataaaa aggatctcct tttttcccag   3240
cccaaattct cctctctaaa agtgtccaca agaaggggtg tttattcttc caacacattt   3300
cacttttctg taaatataca taaacttaaa aagaaaacct catggagtca tcttgcacac   3360
actttcatgc agtgctcttt gtagctaaca gtgaagattt acctcgttct gctcagaggc   3420
cttgctgtgg agctccactg ccatgtaccc agtagggttt gacatttcat tagccatgca   3480
acatggatat gtattgggca gcagactgtg tttcgtgaac tgcagtgatg tatacatctt   3540
atagatgcaa agtattttgg ggtatattat cctaagggaa gataaagatg atattaagaa   3600
ctgctgtttc acggggccct tacctgtgac cctctttgct gaagaatatt taaccccaca   3660
cagcacttca aagaagctgt cttggaagtc tgtctcagga gcaccctgtc ttcttaattc   3720
tccaagcgga tgctccattt caattgcttt gtgacttctt cttctttgtt ttttaaata   3780 ttatgctgct ttaacagtgg agctgaattt tctggaaaat gcttcttggc tggggccact   3840
acctcctttc ctatctttac atctatgtgt atgttgactt tttaaaattc tgagtgatcc   3900
agggtatgac ctagggaatg aactagctat gaaatactca gggttaggaa tcctagcact   3960
tgtctcagga ctctgaaaag gaacggcttc ctcattcctt gtcttgataa agtggaattg   4020
gcaaactaga atttagtttg tactcagtgg acagtgctgt tgaagatttg aggacttgtt   4080
aaagagcact gggtcatatg gaaaaaatgt atgtgtctcc caggtgcatt tcttggttta   4140
tgtcttgttc ttgagatttt gtatatttag gaaaacctca agcagtaatt aatatctcct   4200
ggaacactat agagaaccaa gtgaccgact catttacaac tgaaacctag gaagcccctg   4260
agtcctgagc gaaaacagga gagttagtcg ccctacagga aacccagcta gactattggg   4320
tatgaactaa aaagagactg tgccatggtg agaaaaatgt aaaatcctac agtggaatga   4380
gcagccctta cagtgttgtt accaccaagg gcaggtaggt attagtgttt gaaaaagctg   4440
gtctttgagc gagggcataa atacagctag ccccaggggt ggaacaactg tgggagtctt   4500
gggtactcgc acctcttggc tttgttgatg ctccgccagg aaggccactt gtgtgtgcgt   4560
gtcagttact ttttttagtaa caattcagat ccagtgtaaa cttccgttca ttgctctcca   4620
gtcacatgcc cccacttccc cacaggtgaa agttttttctg aaagtgttgg gattggttaa   4680
```

```
ggtctttatt tgtattacgt atctccccaa gtcctctgtg gccagctgca tctgtctgaa    4740
tggtgcgtga aggctctcag acctacaca ccattttgta agttatgttt tacatgcccc    4800
gtttttgaga ctgatctcga tgcaggtgga tctccttgag atcctgatag cctgttacag    4860
gaatgaagta aaggtcagtt tttttttgtat tgattttcac agctttgagg aacatgcata    4920
agaaatgtag ctgaagtaga ggggacgtga gagaagggcc aggccggcag ccaacccctc    4980
ctccaatgga aattcccgtg ttgcttcaaa ctgagacaga tgggacttaa caggcaatgg    5040
ggtccacttc cccctcttca gcatcccccg taccccactt tttgctgaaa gaactgccag    5100
caggtaggac cccagaggcc cccaaatgaa agcttgaatt tccccctactg gctctgcgtt    5160 ttgctgagat ctgtaggaaa ggatgcttca caaactgagg tagataatgc tatgctgtcg    5220
ttggtataca tcatgaattt ttatgtaaat tgctctgcaa agcaaattga tatgtttgat    5280
aaatttatgt ttttaggtaa ataaaaactt ttaaaaagtt gtt                    5323
```

<210> SEQ ID NO 4
<211> LENGTH: 450
<212> TYPE: PRT
<213> ORGANISM: Artificial Sequence
<220> FEATURE:
<223> OTHER INFORMATION: Synthetic construct

<400> SEQUENCE: 4

```
Met Asn Leu Glu Gly Gly Gly Arg Gly Gly Glu Phe Gly Met Ser Ala
1               5                   10                  15

Val Ser Cys Gly Asn Gly Lys Leu Arg Gln Trp Leu Ile Asp Gln Ile
            20                  25                  30

Asp Ser Gly Lys Tyr Pro Gly Leu Val Trp Glu Asn Glu Glu Lys Ser
        35                  40                  45

Ile Phe Arg Ile Pro Trp Lys His Ala Gly Lys Gln Asp Tyr Asn Arg
    50                  55                  60

Glu Glu Asp Ala Ala Leu Phe Lys Ala Trp Ala Leu Phe Lys Gly Lys
65                  70                  75                  80

Phe Arg Glu Gly Ile Asp Lys Pro Asp Pro Thr Trp Lys Thr Arg
                85                  90                  95

Leu Arg Cys Ala Leu Asn Lys Ser Asn Asp Phe Glu Glu Leu Val Glu
            100                 105                 110

Arg Ser Gln Leu Asp Ile Ser Asp Pro Tyr Lys Val Tyr Arg Ile Val
        115                 120                 125

Pro Glu Gly Ala Lys Lys Gly Ala Lys Gln Leu Thr Leu Glu Asp Pro
    130                 135                 140

Gln Met Ser Met Ser His Pro Tyr Thr Met Thr Thr Pro Tyr Pro Ser
145                 150                 155                 160

Leu Pro Ala Gln Val His Asn Tyr Met Met Pro Leu Asp Arg Ser
                165                 170                 175

Trp Arg Asp Tyr Val Pro Asp Gln Pro His Pro Glu Ile Pro Tyr Gln
            180                 185                 190

Cys Pro Met Thr Phe Gly Pro Arg Gly His His Trp Gln Gly Pro Ala
        195                 200                 205

Cys Glu Asn Gly Cys Gln Val Thr Gly Thr Phe Tyr Ala Cys Ala Pro
    210                 215                 220

Pro Glu Ser Gln Ala Pro Gly Val Pro Thr Glu Pro Ser Ile Arg Ser
225                 230                 235                 240

Ala Glu Ala Leu Ala Phe Ser Asp Cys Arg Leu His Ile Cys Leu Tyr
                245                 250                 255
```

Tyr Arg Glu Ile Leu Val Lys Glu Leu Thr Thr Ser Ser Pro Glu Gly
                260                 265                 270

Cys Arg Ile Ser His Gly His Thr Tyr Asp Ala Ser Asn Leu Asp Gln
            275                 280                 285

Val Leu Phe Pro Tyr Pro Glu Asp Asn Gly Gln Arg Lys Asn Ile Glu
        290                 295                 300

Lys Leu Leu Ser His Leu Glu Arg Gly Val Val Leu Trp Met Ala Pro
305                 310                 315                 320

Asp Gly Leu Tyr Ala Lys Arg Leu Cys Gln Ser Arg Ile Tyr Trp Asp
                325                 330                 335

Gly Pro Leu Ala Leu Cys Asn Asp Arg Pro Asn Lys Leu Glu Arg Asp
            340                 345                 350

Gln Thr Cys Lys Leu Phe Asp Thr Gln Gln Phe Leu Ser Glu Leu Gln
        355                 360                 365

Ala Phe Ala His His Gly Arg Ser Leu Pro Arg Phe Gln Val Thr Leu
    370                 375                 380

Cys Phe Gly Glu Glu Phe Pro Asp Pro Gln Arg Gln Arg Lys Leu Ile
385                 390                 395                 400

Thr Ala His Val Glu Pro Leu Leu Ala Arg Gln Leu Tyr Tyr Phe Ala
                405                 410                 415

Gln Gln Asn Ser Gly His Phe Leu Arg Gly Tyr Asp Leu Pro Glu His
            420                 425                 430

Ile Ser Asn Pro Glu Asp Tyr His Arg Ser Ile Arg His Ser Ser Ile
        435                 440                 445

Gln Glu
    450

<210> SEQ ID NO 5
<211> LENGTH: 1353
<212> TYPE: DNA
<213> ORGANISM: Artificial Sequence
<220> FEATURE:
<223> OTHER INFORMATION: Synthetic construct

<400> SEQUENCE: 5
atgaacctgg agggcggcgg ccgaggcgga gagttcggca tgagcgcggt gagctgcggc      60
aacgggaagc tccgccagtg gctgatcgac cagatcgaca cggcaagta cccccgggctg     120 gtgtgggaga cgaggagaa gagcatcttc cgcatcccct ggaagcacgc gggcaagcag     180
gactacaacc gcgaggagga cgccgcgctc ttcaaggctt gggcactgtt taaaggaaag     240
ttccgagaag gcatcgacaa gccggaccct cccacctgga agacgcgcct gcggtgcgct     300
ttgaacaaga gcaatgactt tgaggaactg gttgagcgga gccagctgga catctcagac     360
ccgtacaaag tgtacaggat tgttcctgag ggagccaaaa aaggagccaa gcagctcacc     420
ctggaggacc gcagatgtc catgagccac ccctacacca tgacaacgcc ttacccttcg     480
ctcccagccc aggttcacaa ctacatgatg ccacccctcg accgaagctg agggactac      540 gtcccggatc agccacaccc ggaaatcccg taccaatgtc ccatgacgtt tggaccccgc     600
ggccaccact ggcaaggccc agcttgtgaa aatggttgcc aggtgacagg aaccttttat     660
gcttgtgccc cacctgagtc ccaggctccc ggagtcccca cagagccaag cataaggtct     720
gccgaagcct ggcgttctc agactgccgg ctgcacatct gcctgtacta ccgggaaatc     780
ctcgtgaagg agctgaccac gtccagcccc gagggctgcc ggatctccca tggacatacg     840
tatgacgcca gcaacctgga ccaggtcctg ttcccctacc agaggacaa tggccagagg     900

```
aaaaacattg agaagctgct gagccacctg gagaggggcg tggtcctctg gatggccccc    960
gacgggctct atgcgaaaag actgtgccag agcaggatct actgggacgg gcccctggcg   1020
ctgtgcaacg accggcccaa caaactggag agagaccaga cctgcaagct ctttgacaca   1080
cagcagttct tgtcagagct gcaagcgttt gctcaccacg gccgctccct gccaagattc   1140
caggtgactc tatgctttgg agaggagttt ccagaccctc agaggcaaag aaagctcatc   1200
acagctcacg tagaacctct gctagccaga caactatatt attttgctca acaaaacagt   1260
ggacatttcc tgaggggcta cgatttacca gaacacatca gcaatccaga agattaccac   1320
agatctatcc gccattcctc tattcaagaa tga                                1353

<210> SEQ ID NO 6
<211> LENGTH: 5320
<212> TYPE: DNA
<213> ORGANISM: Artificial Sequence
<220> FEATURE:
<223> OTHER INFORMATION: Synthetic construct

<400> SEQUENCE: 6
acctcgcact ctcagtttca ccgctcgatc ttgggaccca ccgctgccct cagctccgag     60
tccagggcga gtgcagagca gagcgggcgg aggaccccgg gcgcgggcgc ggacggcacg    120
cgggcatgaa cctggagggc ggcggccgag gcggagagtt cggcatgagc gcggtgagct    180
gcggcaacgg gaagctccgc cagtggctga tcgaccagat cgacagcggc aagtaccccg    240
ggctggtgtg ggagaacgag gagaagagca tcttccgcat cccctggaag cacgcgggca    300
agcaggacta caaccgcgag gaggacgccg cgctcttcaa ggcttgggca ctgtttaaag    360
gaaagttccg agaaggcatc gacaagccgg accctcccac ctggaagacg cgcctgcggt    420
gcgctttgaa caagagcaat gactttgagg aactggttga gcggagccag ctggacatct    480
cagacccgta caaagtgtac aggattgttc ctgagggagc caaaaaagga gccaagcagc    540
tcaccctgga ggacccgcag atgtccatga gccacccta ccatgacaa cgccttacc     600 cttcgctccc agcccaggtt cacaactaca tgatgccacc cctcgaccga agctggaggg    660
actacgtccc ggatcagcca caccccggaaa tcccgtacca atgtcccatg acgtttggac    720
cccgcggcca ccactggcaa ggcccagctt gtgaaaatgg ttgccaggtg acaggaacct    780
tttatgcttg tgccccacct gagtcccagg ctcccggagt ccccacagag ccaagcataa    840
ggtctgccga agccttggcg ttctcagact gccggctgca catctgcctg tactaccggg    900
aaatcctcgt gaaggagctg accacgtcca gccccgaggg ctgccggatc tcccatggac    960
atacgtatga cgccagcaac ctggaccagg tcctgttccc ctacccagag acaatggcc    1020 agaggaaaaa cattgagaag ctgctgagcc acctggagag gggcgtggtc ctctggatgg    1080
cccccgacgg gctctatgcg aaaagactgt gccagagcag gatctactgg gacgggcccc    1140
tggcgctgtg caacgaccgg cccaacaaac tggagagaga ccagacctgc aagtctcttg    1200
acacacagca gttcttgtca gagctgcaag cgtttgctca ccacggccgc tccctgccaa    1260
gattccaggt gactctatgc tttggagagg agtttccaga ccctcagagg caaagaaagc    1320
tcatcacagc tcacgtagaa cctctgctag ccagacaact atattatttt gctcaacaaa    1380
acagtggaca tttcctgagg ggctacgatt taccagaaca catcagcaat ccagaagatt    1440
accacagatc tatccgccat tcctctattc aagaatgaaa aatgtcaaga tgagtggttt    1500 tcttttttcct ttttttttt tttttttgat acggggatac ggggtcttgc tctgtctccc    1560
```

```
aggctggagt gcagtgacac aatctcagct cactgtgacc tccgcctcct gggttcaaga    1620
gactctcctg cctcagcctc cctggtagct gggattacag gtgtgagcca ctgcacccac    1680
ccaagacaag tgattttcat tgtaaatatt tgactttagt gaaagcgtcc aattgactgc    1740
cctcttactt ttttgaggaa ctcagaagtg gagatttcag ttcagcggtt gaggagaatt    1800
gcggcgagac aagcatggaa aatcagtgac atctgattgg cagatgagct tatttcaaaa    1860
ggaagggtgg cttttgcattt cttgtgttct atagactgcc atcattgatg atcactgtga    1920
aaattgacca agtgatgtgt ttacatttac tgaaatgtgc tctttaatttt gttgtagatt    1980 aggtcttgct ggaagacaga gaaaacttgc ctttcagtat tgacactgac tagagtgatg    2040
actgcttgta ggtatgtctg tgccatttct cagggaagta agatgtaaat tgaagaagcc    2100
tcacacgtaa aagaaatgta ttaatgtatg taggagctgc agttcttgtg gaagacactt    2160
gctgagtgaa ggaaatgaat ctttgactga agccgtgcct gtagccttgg ggaggcccat    2220
cccccacctg ccagcggttt cctggtgtgg gtccctctgc cccaccctcc ttcccattgg    2280 cttttctctcc ttggcctttc ctggaagcca gttagtaaac ttcctatttt cttgagtcaa    2340
aaaacatgag cgctactctt ggatgggaca ttttttgtctg tcctacaatc tagtaatgtc    2400
taagtaatgg ttaagttttc ttgtttctgc atcttttttga ccctcattct ttagagatgc    2460
taaaattctt cgcataaaga agaagaaatt aaggaacata aatcttaata cttgaactgt    2520
tgcccttctg tccaagtact taactatctg ttcccttcct ctgtgccacg ctcctctgtt    2580
tgcttggctg tccagcgatc agccatggcg acactaaagg aggaggagcc ggggactccc    2640
aggctggaga gcactgccag gacccaccac tggaagcagg atggagctga ctacggaact    2700
gcacactcag tgggctgttt ctgcttattt catctgttct atgcttcctc gtgccaatta    2760
tagtttgaca gggccttaaa attacttggc ttttttccaaa tgcttctatt tatagaatcc    2820
caaagacctc cacttgctta agtataccta tcacttacat ttttgtggtt ttgagaaagt    2880
acagcagtag actggggcgt cacctccagg ccgtttctca tactacagga tatttactat    2940
tactcccagg atcagcagaa gattgcgtag ctctcaaatg tgtgttcctg cttttctaat    3000
ggatatttta aattcattca acaagcacct agtaagtgcc tgctgtatcc ctacattaca    3060
cagttcagcc tttatcaagc ttagtgagca gtgagcactg aaacattatt ttttaatgtt    3120
taaaaagttt ctaatattaa agtcagaata ttaatacaat taatattaat attaactaca    3180
gaaaagacaa acagtagaga acagcaaaaa aataaaaagg atctcctttt ttcccagccc    3240
aaattctcct ctctaaaagt gtccacaaga aggggtgttt attcttccaa cacatttcac    3300
ttttctgtaa atatacataa acttaaaaag aaaacctcat ggagtcatct tgcacacact    3360
ttcatgcagt gctctttgta gctaacagtg aagatttacc tcgttctgct cagaggcctt    3420
gctgtggagc tccactgcca tgtacccagt agggtttgac atttcattag ccatgcaaca    3480
tggatatgta ttgggcagca gactgtgttt cgtgaactgc agtgatgtat acatcttata    3540
gatgcaaagt attttgggggt atattatcct aagggaagat aaagatgata ttaagaactg    3600
ctgtttcacg gggcccttac ctgtgaccct cttttgctgaa gaatatttaa ccccacacag    3660
cacttcaaag aagctgtctt ggaagtctgt ctcaggagca ccctgtcttc ttaattctcc    3720
aagcggatgc tccatttcaa ttgctttgtg acttcttctt ctttgttttt ttaaatatta    3780
tgctgcttta acagtggagc tgaatttttct ggaaaatgct tcttggctgg ggccactacc    3840 tccttttccta tctttacatc tatgtgtatg ttgacttttt aaaattctga gtgatccagg    3900
gtatgaccta gggaatgaac tagctatgaa atactcaggg ttaggaatcc tagcacttgt    3960
```

```
ctcaggactc tgaaaaggaa cggcttcctc attccttgtc ttgataaagt ggaattggca    4020
aactagaatt tagtttgtac tcagtggaca gtgctgttga agatttgagg acttgttaaa    4080
gagcactggg tcatatggaa aaaatgtatg tgtctcccag gtgcatttct tggtttatgt    4140
cttgttcttg agattttgta tatttaggaa aacctcaagc agtaattaat atctcctgga    4200
acactataga gaaccaagtg accgactcat ttacaactga aacctaggaa gccctgagt     4260 cctgagcgaa aacaggagag ttagtcgccc tacaggaaac ccagctagac tattgggtat    4320
gaactaaaaa gagactgtgc catggtgaga aaaatgtaaa atcctacagt ggaatgagca    4380
gcccttacag tgttgttacc accaagggca ggtaggtatt agtgtttgaa aaagctggtc    4440
tttgagcgag ggcataaata cagctagccc cagggtgga acaactgtgg gagtcttggg     4500
tactcgcacc tcttggcttt gttgatgctc cgccaggaag gccacttgtg tgtgcgtgtc    4560
agttactttt ttagtaacaa ttcagatcca gtgtaaactt ccgttcattg ctctccagtc    4620
acatgccccc acttccccac aggtgaaagt ttttctgaaa gtgttgggat tggttaaggt    4680
ctttatttgt attacgtatc tccccaagtc ctctgtggcc agctgcatct gtctgaatgg    4740
tgcgtgaagg ctctcagacc ttacacacca tttgtaagt tatgttttac atgccccgtt     4800
tttgagactg atctcgatgc aggtggatct ccttgagatc ctgatagcct gttacaggaa    4860
tgaagtaaag gtcagttttt tttgtattga ttttcacagc tttgaggaac atgcataaga    4920
aatgtagctg aagtagaggg gacgtgagag aagggccagg ccggcaggcc aaccctcctc    4980
caatggaaat tcccgtgttg cttcaaactg agacagatgg gacttaacag gcaatggggt    5040
ccacttcccc ctcttcagca tccccgtac cccactttt gctgaaagaa ctgccagcag      5100
gtaggacccc agaggccccc aaatgaaagc ttgaatttcc cctactggct ctgcgttttg    5160
ctgagatctg taggaaagga tgcttcacaa actgaggtag ataatgctat gctgtcgttg    5220
gtatacatca tgaatttta tgtaaattgc tctgcaaagc aaattgatat gtttgataaa     5280
tttatgtttt taggtaaata aaacttttta aaaagttgtt                          5320
```